United States Patent
Leduc et al.

(10) Patent No.: US 8,083,809 B2
(45) Date of Patent: Dec. 27, 2011

(54) AZOMETHINE DIRECT DYES OR REDUCED PRECURSORS OF THESE DYES OBTAINED FROM 2-CHLORO-3-AMINO-6-METHYLPHENOL, AND HAIR DYEING METHOD STARTING FROM THESE DYES AND PRECURSORS

(75) Inventors: Madeleine Leduc, Paris (FR); Stéphane Sabelle, Paris (FR); Eric Metais, St Leu la Forêt (FR); Christophe Rondot, Mitry-mory (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/808,100

(22) PCT Filed: Dec. 9, 2008

(86) PCT No.: PCT/EP2008/067152
§ 371 (c)(1),
(2), (4) Date: Sep. 23, 2010

(87) PCT Pub. No.: WO2009/077393
PCT Pub. Date: Jun. 25, 2009

(65) Prior Publication Data
US 2011/0041261 A1 Feb. 24, 2011

Related U.S. Application Data

(60) Provisional application No. 61/006,279, filed on Jan. 4, 2008.

(30) Foreign Application Priority Data

Dec. 14, 2007 (FR) ...................... 07 59848

(51) Int. Cl.
*A61Q 5/10* (2006.01)
*C07C 50/04* (2006.01)
(52) U.S. Cl. .......... 8/405; 8/406; 8/410; 8/435; 552/302
(58) Field of Classification Search ............... 8/405, 406, 8/410, 435; 552/302
See application file for complete search history.

(56) References Cited

U.S. PATENT DOCUMENTS

| | | | |
|---|---|---|---|
| 3,838,965 A | 10/1974 | Kalopissis et al. | |
| 3,884,625 A | 5/1975 | Kalopissis et al. | |
| 3,893,802 A | 7/1975 | Kalopissis et al. | |
| 3,929,403 A | 12/1975 | Kalopissis et al. | |
| 3,956,342 A | 5/1976 | Kalopissis et al. | |
| 4,093,806 A * | 6/1978 | Kalopissis et al. | 544/165 |
| 4,222,958 A * | 9/1980 | Kalopissis et al. | 564/50 |
| 4,246,181 A | 1/1981 | Kalopissis et al. | |
| 4,675,130 A | 6/1987 | Kalopissis et al. | |
| 5,900,028 A | 5/1999 | Audousset | |

FOREIGN PATENT DOCUMENTS

| | | |
|---|---|---|
| EP | 0 766 958 | 4/1997 |
| EP | 1 398 021 A1 | 3/2004 |
| FR | 2 047 932 | 3/1971 |
| FR | 2 101 603 | 3/1972 |
| FR | 2 234 277 | 1/1975 |
| FR | 2 262 023 | 9/1975 |

OTHER PUBLICATIONS

STIC Search Report dated Feb. 23, 2011.*
International Search Report for PCT/EP2008/067152, dated May 6, 2009.
Office Action dated Apr. 28, 2011, in U.S. Appl. No. 12/808,111.
STIC Search Report for U.S. Appl. No. 12/808,111, dated Feb. 23, 2011.

* cited by examiner

*Primary Examiner* — Eisa Elhilo
(74) *Attorney, Agent, or Firm* — Finnegan, Henderson, Garrett & Dunner, LLP

(57) ABSTRACT

The invention relates to the dyeing of keratinous fibres using azomethine direct dyes of formula (I) or reduced precursors of azomethine direct dyes of formula (II) obtained from 2-chloro-3-amino-6-methylphenol. A subject-matter of the invention is a dyeing composition comprising at least one chlorinated azomethine direct dye or one reduced precursor of a chlorinated azomethine direct dye, a method for dyeing keratinous fibres which employs the said composition and their uses in the dyeing of keratinous fibres. This composition makes it possible to obtain a particularly stable and consistent colouring.

16 Claims, No Drawings

AZOMETHINE DIRECT DYES OR REDUCED PRECURSORS OF THESE DYES OBTAINED FROM 2-CHLORO-3-AMINO-6-METHYLPHENOL, AND HAIR DYEING METHOD STARTING FROM THESE DYES AND PRECURSORS

CROSS REFERENCE TO RELATED APPLICATIONS

This application is a national phase application based on PCT/EP2008/067152, filed Dec. 9, 2008, which claims the priority of French Patent Application No. 0759848, filed Dec. 14, 2007, and claims the benefit of U.S. Provisional Application No. 61/006,279, filed Jan. 4, 2008, the content of all of which is incorporated herein by reference.

The invention relates to the dyeing of keratinous fibres using azomethine direct dyes or reduced precursors of azomethine direct dyes obtained from 2-chloro-3-amino-6-methylphenol.

It is known to dye keratinous fibres and in particular the hair, with dyeing compositions comprising direct dyes, according to a "direct dyeing" method.

The method conventionally used in direct dyeing consists in applying, to the keratinous fibres, direct dyes or colouring molecules having affinity for the said fibres, in leaving them to stand and then rinsing the fibres. The direct dyes used to date are nitrobenzene dyes, anthraquinones, nitropyridines or dyes of azo, xanthene, acridine, azine or triarylmethane benzene derivative type.

Other dyes result from oxidation bases and oxidation couplers which, once condensed, are applied to the hair. For example, in the documents FR 233 036, FR 2 262 022, FR 2 262 024, U.S. Pat. No. 4,221,729 and FR 2 261 750, diphenylamines, such as leuco derivatives of indophenols, of indamine and of indoaniline, are used, either alone or in combination with other dyes, in dyeing compositions. Other compounds corresponding to oxidized derivatives of leuco derivatives, such as those described in the documents FR 2 254 557 and FR 2 234 277, are also known to dye keratinous fibres.

The colourings which result from direct dyeings are temporary or semi-permanent colourings, as the nature of the interactions which bind direct dyes to the keratinous fibre and their desorption from the surface and/or from the core of the fibre are responsible for their low dyeing power and for their poor hold with regard to washing operations or to perspiration. In addition, these direct dyes are generally sensitive to the action of oxidizing agents, such as aqueous hydrogen peroxide solution, which renders them generally unusable in lightening direct dyeing compositions based on aqueous hydrogen peroxide solution and on a basifying agent, which will be similar to oxidation dyeings.

Direct dyes also exhibit a certain lack of stability towards light related to the low resistance of the chromophore with regard to photochemical attacks. In addition, their sensitivity to light is dependent on the distribution of their molecules, uniform or aggregated, in the substrate.

Consequently, there exists a real need to find direct dyes which make it possible to dye keratinous fibres, which are stable towards light, which are also resistant to bad weather, to washing operations and to perspiration, and which are sufficiently stable in the presence of oxidizing agents, such as aqueous hydrogen peroxide solution, to be able to obtain simultaneous lightening of the fibre with the advantages set out above, while exhibiting an improved toxicological profile compatible with cosmetic use on keratinous fibres.

These aims are achieved with the present invention, a subject-matter of which is a method for dyeing keratinous fibres starting from the direct dyes of formula (I):

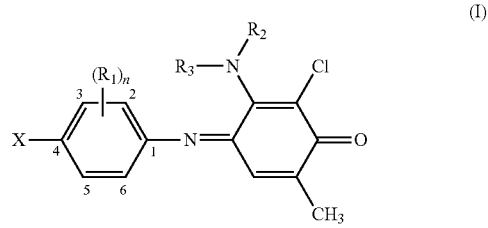

their organic or inorganic acid salts, their geometrical isomers, their tautomers and their solvates, such as hydrates;

in which formula (I):

$R_1$ represents:
 a chlorine atom;
 a $(C_1-C_3)$alkyl radical optionally substituted by one or more hydroxyl groups;
 a $(C_1-C_3)$alkoxy radical optionally substituted by one or more hydroxyl groups;

X represents:
 a hydroxyl radical;
 an —$NR_4R_5$ radical with $R_4$ and $R_5$ representing, independently of one another:
  i) a hydrogen atom;
  ii) a $C_1-C_5$ alkyl radical optionally substituted by one or more groups chosen from hydroxyl, $(C_1-C_3)$ alkoxy, amino, $(C_1-C_3)$ alkylamino, di$(C_1-C_3)$ alkylamino, aminocarbonyl, carboxyl —COOH, sulpho —$SO_3H$, tri$(C_1-C_3)$alkylammonio and $(C_1-C_3)$alkylimidazolio;
  a pyrrolidinyl radical optionally substituted by a group chosen from hydroxyl, $(C_1-C_3)$alkoxy, amino, $(C_1-C_3)$alkylamino, di$(C_1-C_3)$alkylamino, tri$(C_1-C_3)$ alkylammonio and $(C_1-C_3)$ alkylimidazolio;
  a piperidinyl radical optionally substituted by a group chosen from hydroxyl, $(C_1-C_3)$alkoxy, amino, $(C_1-C_3)$alkylamino, di$(C_1-C_3)$alkylamino, tri$(C_1-C_3)$ alkylammonio and $(C_1-C_3)$alkylimidazolio;

n represents an integer between 0 and 3 inclusive;

$R_2$ and $R_3$, which are identical or different, are as defined for $R_4$ and $R_5$;

it being understood that, when X and/or $R_2$ and/or $R_3$ and/or $R_4$ and/or $R_5$ comprise a cationic group, the electrical neutrality of the compounds of formula (I) is brought about by a cosmetically acceptable anionic counterion or a mixture of cosmetically acceptable anionic counterions, such as, for example, chlorides, bromides and sulphates.

Another subject-matter of the invention is a dyeing method starting from colourless reduced precursors of chlorinated azomethine dyes which, once oxidized, generate the compounds of formula (I) as defined above. These precursors correspond to the compounds of formula (II):

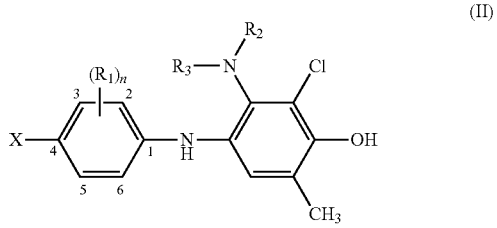

their organic or inorganic acid salts, their geometrical isomers, their tautomers and their solvates, such as hydrates; in which formula (II) $R_1$, $R_2$, $R_3$, X and n are as defined above; it being understood that:

when X and/or $R_2$ and/or $R_3$ and/or $R_4$ and/or $R_5$ comprise a cationic group, the electrical neutrality of the compounds of formula (II) is brought about by a cosmetically acceptable anionic counterion or a mixture of cosmetically acceptable anionic counterions, such as, for example, chlorides, bromides and sulphates.

Another subject-matter of the invention is a compound of formula (I) or (II) as defined above.

Another subject-matter of the invention is a dyeing composition for the dyeing of keratinous fibres comprising, in a cosmetic medium, at least one compound of formula (I) or (II) as defined above.

The direct dyes of formula (I) make it possible to overcome the disadvantages of the direct dyes conventionally used previously and result in dyeings by direct dyeing which have very good resistance to light, to bad weather, to washing operations, to perspiration and to rubbing actions. Their good stability with regard to oxidizing agents, such as aqueous hydrogen peroxide solution, also makes it possible to use them in a lightening direct dyeing method.

Furthermore, it has been discovered that the reduced form of the azomethine derivatives obtained from 2-chloro-3-amino-6-methylphenol derivatives of formula (II), used under oxidizing conditions, can also result in colourings having very good resistance to light, to bad weather, to washing operations, to perspiration and to rubbing actions.

Within the meaning of the present invention and unless otherwise indicated:

an "organic or inorganic acid salt" is, for example, chosen from a salt derived i) from hydrochloric acid HCl, ii) from hydrobromic acid HBr, iii) from sulphuric acid $H_2SO_4$, iv) from alkylsulphonic acids: Alk-S(O)$_2$OH, such as methylsulphonic acid and ethylsulphonic acid; v) from arylsulphonic acids: Ar—S(O)$_2$OH, such as benzenesulphonic acid and toluenesulphonic acid; vi) from citric acid; vii) from succinic acid; viii) from tartaric acid; ix) from lactic acid; x) from alkoxysulphinic acids: Alk-O—S(O)OH, such as methoxysulphinic acid and ethoxysulphinic acid; xi) from aryloxysulphinic acids, such as tolyloxysulphinic acid and phenoxysulphinic acid; xii) from phosphoric acid $H_3PO_4$; xiii) from acetic acid $CH_3C(O)OH$; xiv) from triflic acid $CF_3SO_3H$ and xv) from tetrafluoroboric acid $HBF_4$;

an "anionic counterion" is an anion or an anionic group associated with the cationic charge of the dye; more particularly, the anionic counterion is chosen from i) halides, such as chloride or bromide; ii) nitrates; iii) sulphonates, including $C_1$-$C_6$ alkylsulphonates: Alk-S(O)$_2$O$^-$, such as methylsulphonate or mesylate and ethylsulphonate; iv) arylsulphonates: Ar—S(O)$_2$O$^-$, such as benzenesulphonate and toluenesulphonate or tosylate; v) citrate; vi) succinate; vii) tartrate; viii) lactate; ix) alkyl sulphates: Alk-O—S(O)O$^-$, such as methyl sulphate and ethyl sulphate; x) aryl sulphates: Ar—O—S(O)O$^-$, such as phenyl sulphate and tolyl sulphate; xi) alkoxy sulphates: Alk-O—S(O)$_2$O$^-$, such as methoxy sulphate and ethoxy sulphate; xii) aryloxy sulphates: Ar—O—S(O)$_2$O$^-$; xiii) phosphate; xiv) acetate; xv) triflate; and xvi) borates, such as tetrafluoroborate;

an "alkyl" radical is a saturated, linear or branched, hydrocarbon radical comprising from 1 to 6 carbon atoms, particularly from 1 to 3 carbon atoms, such as the methyl or ethyl radical;

an "alkoxy" radical is an "alkyl-oxy" alkyl-O-radical in which the alkyl part is as defined above;

the alkyl, alkoxy or heterocycloalkyl radicals followed by "optionally substituted by . . . " means that the said radicals can have one or more hydrogen atoms replaced by one or more substituents in question, particularly one or two substituents in question.

A subject-matter of the invention is direct dyes of formula (I) or dyeing precursors of formula (II).

A specific embodiment of the invention relates to compounds of formula (I) or (II) for which n has a value zero.

According to another specific embodiment of the invention, the compound or compounds of formula (I) or (II) present in the composition according to the invention are such that n has a value 1 and $R_1$ represents a ($C_1$-$C_3$)alkyl group, such as methyl.

An alternative form relates to compounds of formula (I) or (II) for which X represents a hydroxyl radical.

Another alternative form of the invention resorts to compounds of formula (I) or (II) for which X represents an —$NR_4R_5$ radical with $R_4$ and $R_5$ representing, independently of one another, i) a hydrogen atom or ii) a $C_1$-$C_5$ alkyl radical optionally substituted by one or more groups chosen from hydroxyl, ($C_1$-$C_3$)alkoxy, amino, ($C_1$-$C_3$)alkylamino, di($C_1$-$C_3$)alkylamino, aminocarbonyl, carboxyl —COOH, sulpho —$SO_3H$, tri($C_1$-$C_3$)alkylammonio and ($C_1$-$C_3$)alkylimidazolio. More particularly, X represents a group chosen from: i) (di)($C_1$-$C_3$)(alkyl)amino; ii) (di)[hydroxy($C_1$-$C_3$)alkyl]amino; iii) ($C_1$-$C_3$)alkylimidazolio($C_1$-$C_3$)alkylamino; iv) [N—($C_1$-$C_3$)alkyl, N—($C_1$-$C_3$)alkylimidazolio($C_1$-$C_3$)alkyl]amino; v) tri($C_1$-$C_3$)alkylammonio($C_1$-$C_5$)alkylamino and vi) di[tri($C_1$-$C_3$)alkylammonio($C_1$-$C_5$)alkyl]amino.

According to another specific embodiment of the invention, the compounds of formula (I) or (II) are such that X represents a pyrrolidinyl group optionally substituted by a tri($C_1$-$C_3$)alkylammonio or ($C_1$-$C_3$)alkylimidazolio group. More particularly, X represents a pyrrolidino radical optionally substituted by a tri($C_1$-$C_3$)alkylammonio or ($C_1$-$C_3$)alkylimidazolio group.

According to a specific embodiment, the compounds of formula (I) or (II) are such that $NR_2R_3$ represents an amino $NH_2$ group.

Mention may be made, as example of the compounds of formula (I) or (II) present in the composition according to the invention, of the following dyes (1a) to (1t) and precursors (2a) to (2p), and also their organic or inorganic acid salts, their geometrical isomers, their tautomers and their solvates, such as hydrates:

Dyes of Formula (I):
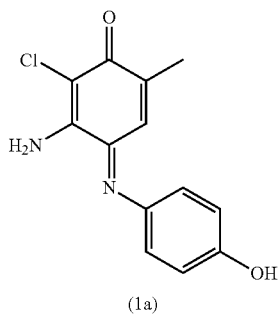
(1a)
3-Amino-2-chloro-4-(4-hydroxyphenylimino)-6-methylcyclohexa-2,5-dienone
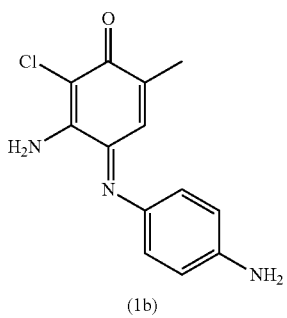
(1b)
3-Amino-4-(4-aminophenylimino)-2-chloro-6-methylcyclohexa-2,5-dienone
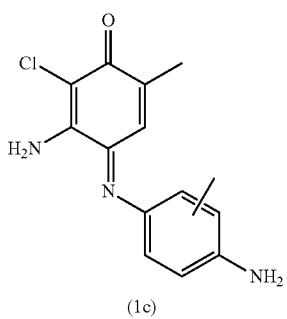
(1c)
3-Amino-4-(4-aminomethylphenylimino)-2-chloro-6-methylcyclohexa-2,5-dienone
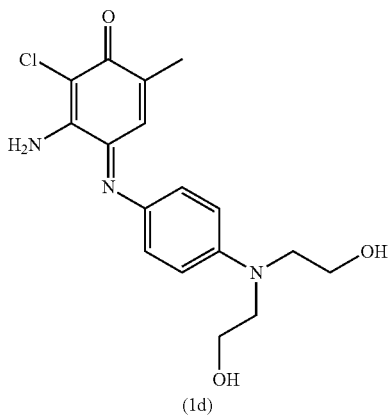
(1d)
3-Amino-4-{4-[bis(2-hydroxyethyl)amino]phenylimino}-2-chloro-6-methylcyclohexa-2,5-dienone

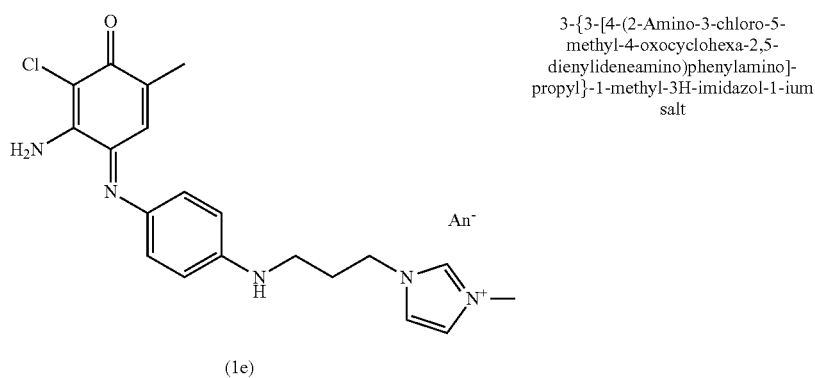

3-{3-[4-(2-Amino-3-chloro-5-methyl-4-oxocyclohexa-2,5-dienylideneamino)phenylamino]-propyl}-1-methyl-3H-imidazol-1-ium salt (1e)

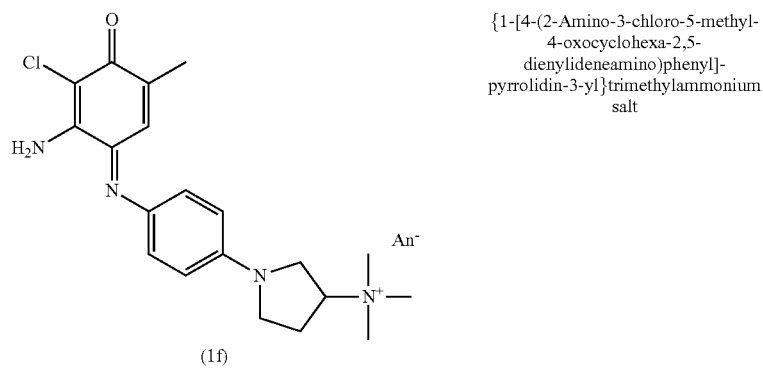

{1-[4-(2-Amino-3-chloro-5-methyl-4-oxocyclohexa-2,5-dienylideneamino)phenyl]-pyrrolidin-3-yl}trimethylammonium salt (1f)

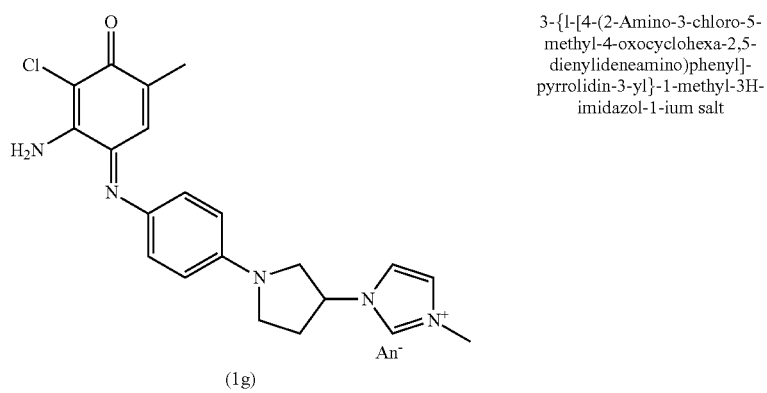

3-{1-[4-(2-Amino-3-chloro-5-methyl-4-oxocyclohexa-2,5-dienylideneamino)phenyl]-pyrrolidin-3-yl}-1-methyl-3H-imidazol-1-ium salt (1g)

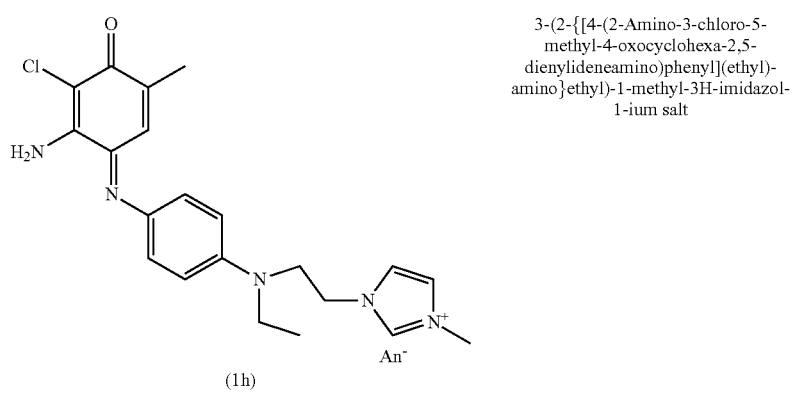

3-(2-{[4-(2-Amino-3-chloro-5-methyl-4-oxocyclohexa-2,5-dienylideneamino)phenyl](ethyl)-amino}ethyl)-1-methyl-3H-imidazol-1-ium salt (1h)

-continued

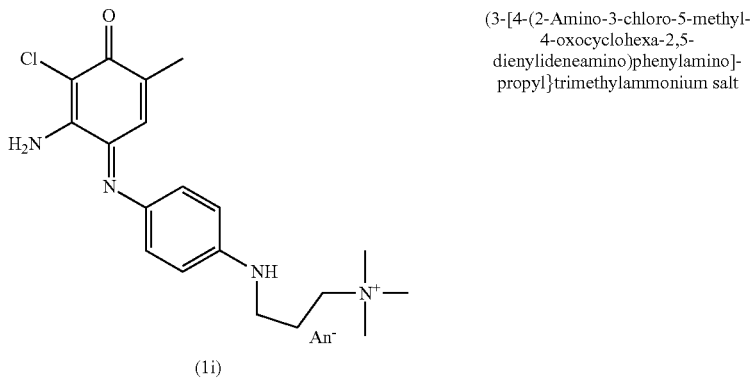

(1i)

(3-[4-(2-Amino-3-chloro-5-methyl-4-oxocyclohexa-2,5-dienylideneamino)phenylamino]-propyl}trimethylammonium salt

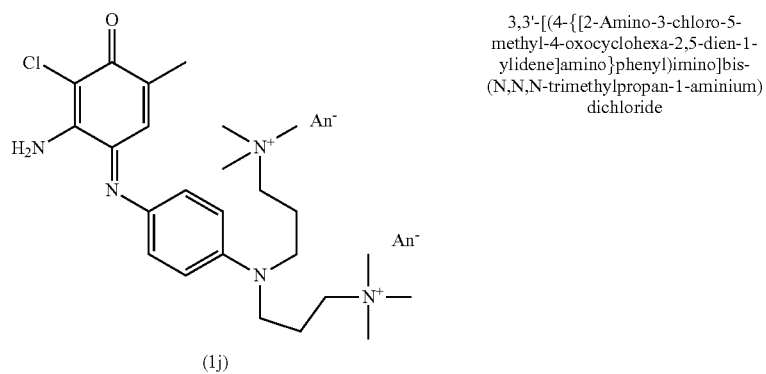

(1j)

3,3'-[(4-{[2-Amino-3-chloro-5-methyl-4-oxocyclohexa-2,5-dien-1-ylidene]amino}phenyl)imino]bis-(N,N,N-trimethylpropan-1-aminium) dichloride

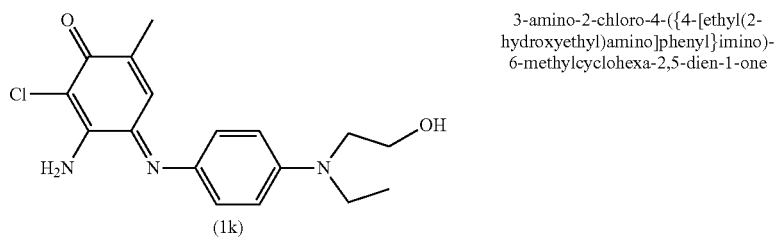

(1k)

3-amino-2-chloro-4-({4-[ethyl(2-hydroxyethyl)amino]phenyl}imino)-6-methylcyclohexa-2,5-dien-1-one

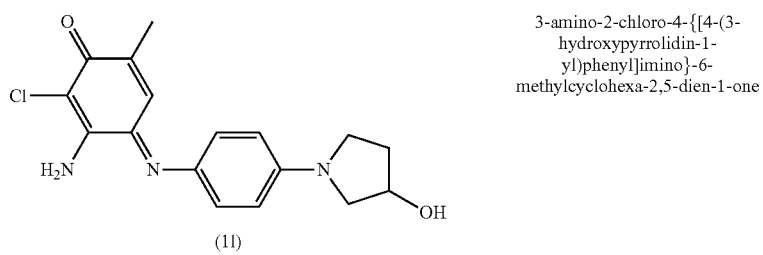

(1l)

3-amino-2-chloro-4-{[4-(3-hydroxypyrrolidin-1-yl)phenyl]imino}-6-methylcyclohexa-2,5-dien-1-one

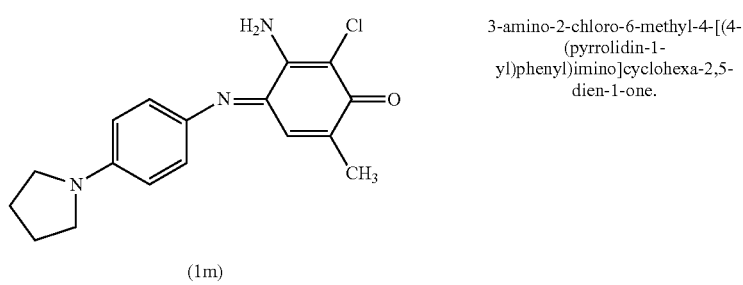

(1m)

3-amino-2-chloro-6-methyl-4-[(4-(pyrrolidin-1-yl)phenyl)imino]cyclohexa-2,5-dien-1-one.

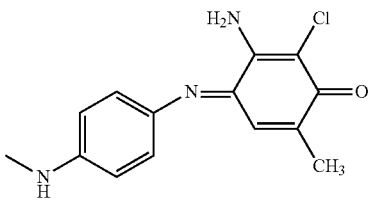

3-amino-2-chloro-6-methyl-4-{[4-(methyl-amino)phenyl]imino}cyclohexa-2,5-dien-1-one (1n)

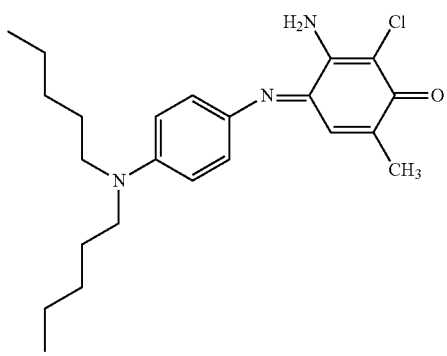

3-amino-2-chloro-4-{[4-(dipentyl-amino)phenyl]imino}-6-methylcyclohexa-2,5-dien-1-one (1p)

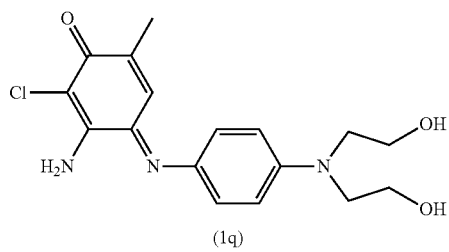

3-amino-4-({4-[bis(2-hydroxy-ethyl)amino]phenyl}imino)-2-chloro-6-methylcyclohexa-2,5-dien-1-one.

(1q)

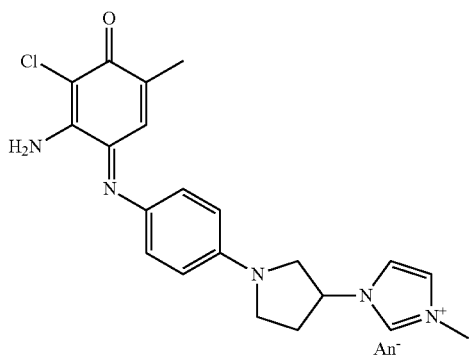

3-{1-[4-(2-amino-3-chloro-5-methyl-4-oxocyclohexa-2,5-dienylideneamino)phenyl]-pyrrolidin-3-yl}-1-methyl-3H-imidazol-1-ium salt (1r)

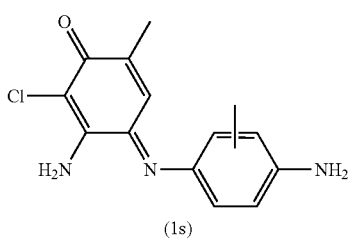

mixture of 3-amino-4-[(4-amino-2 methylphenyl)imino]-2-chloro-6-methylcyclohexa-2,5-dien-1-one and 3-amino-4-[(4-amino-3-methyl-phenyl)imino]-2-chloro-6-methylcyclohexa-2,5-dien-1-one isomers (1s)

-continued
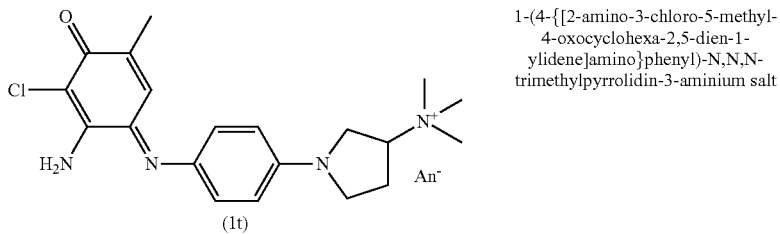
(1t)
1-(4-{[2-amino-3-chloro-5-methyl-4-oxocyclohexa-2,5-dien-1-ylidene]amino}phenyl)-N,N,N-trimethylpyrrolidin-3-aminium salt
Precursors of Formula (II):
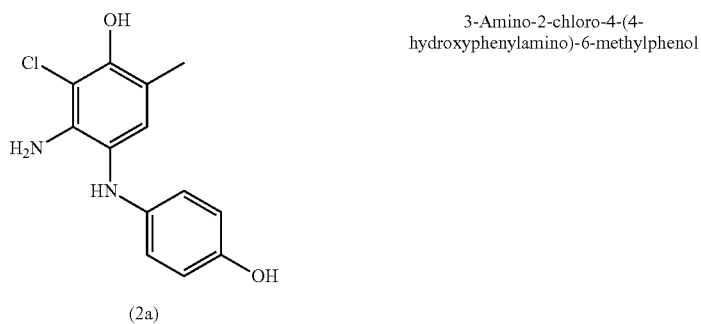
(2a)
3-Amino-2-chloro-4-(4-hydroxyphenylamino)-6-methylphenol
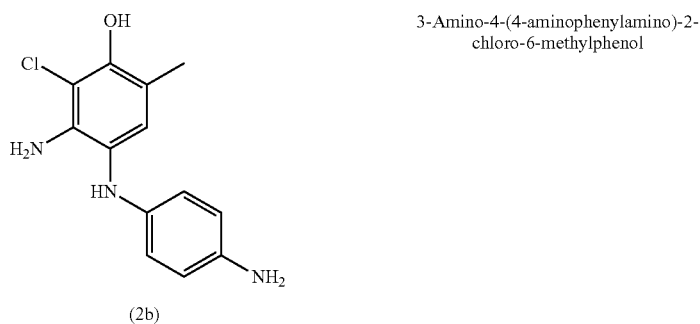
(2b)
3-Amino-4-(4-aminophenylamino)-2-chloro-6-methylphenol
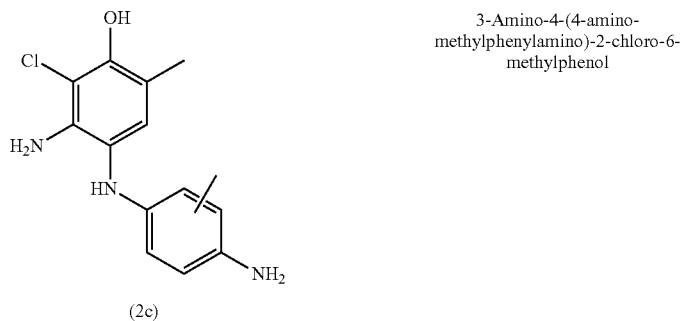
(2c)
3-Amino-4-(4-amino-methylphenylamino)-2-chloro-6-methylphenol

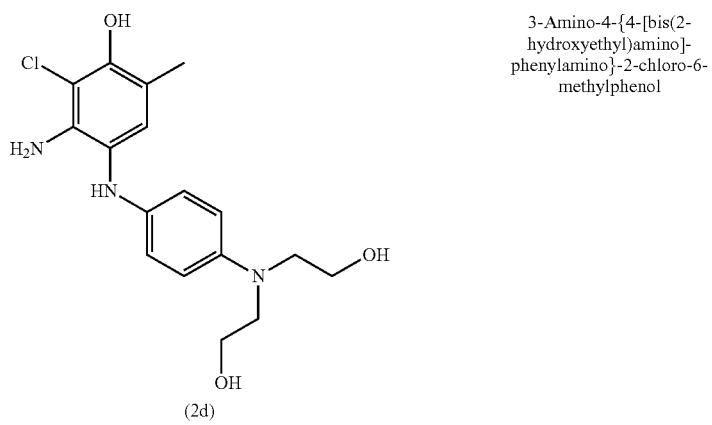
3-Amino-4-{4-[bis(2-hydroxyethyl)amino]-phenylamino}-2-chloro-6-methylphenol
(2d)
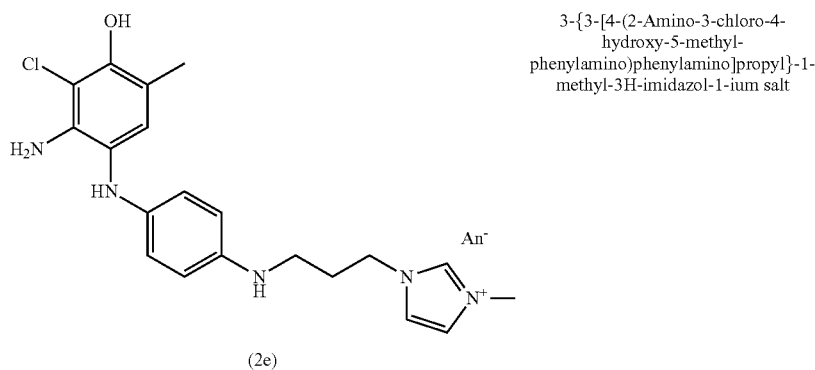
3-{3-[4-(2-Amino-3-chloro-4-hydroxy-5-methyl-phenylamino)phenylamino]propyl}-1-methyl-3H-imidazol-1-ium salt
(2e)
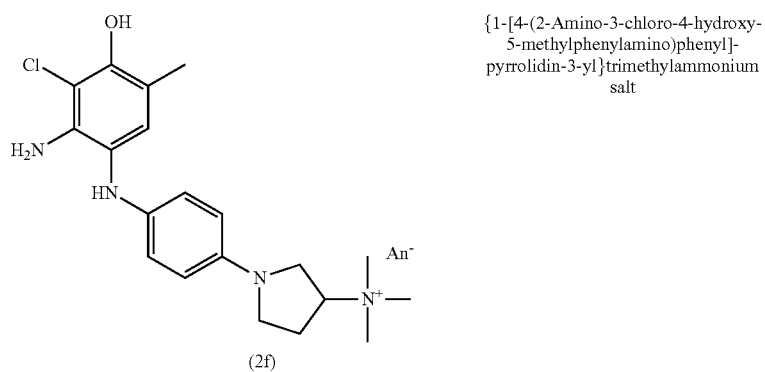
{1-[4-(2-Amino-3-chloro-4-hydroxy-5-methylphenylamino)phenyl]-pyrrolidin-3-yl}trimethylammonium salt
(2f)
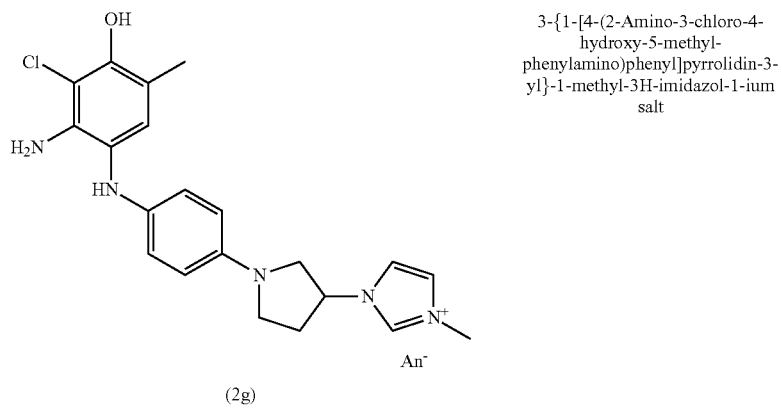
3-{1-[4-(2-Amino-3-chloro-4-hydroxy-5-methyl-phenylamino)phenyl]pyrrolidin-3-yl}-1-methyl-3H-imidazol-1-ium salt
(2g)

-continued
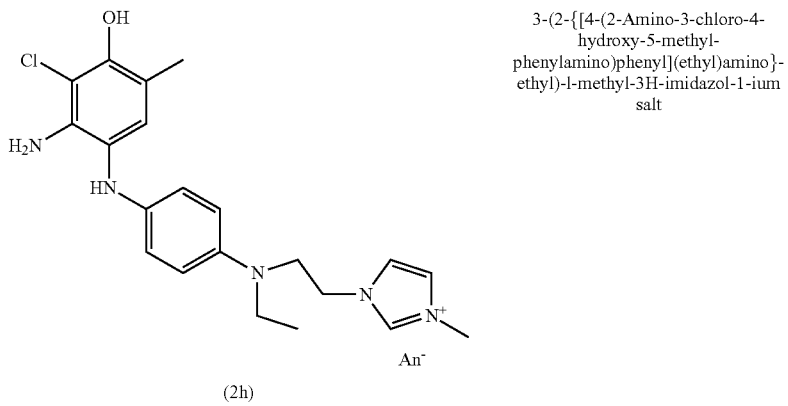
3-(2-{[4-(2-Amino-3-chloro-4-hydroxy-5-methyl-phenylamino)phenyl](ethyl)amino}-ethyl)-1-methyl-3H-imidazol-1-ium salt
(2h)
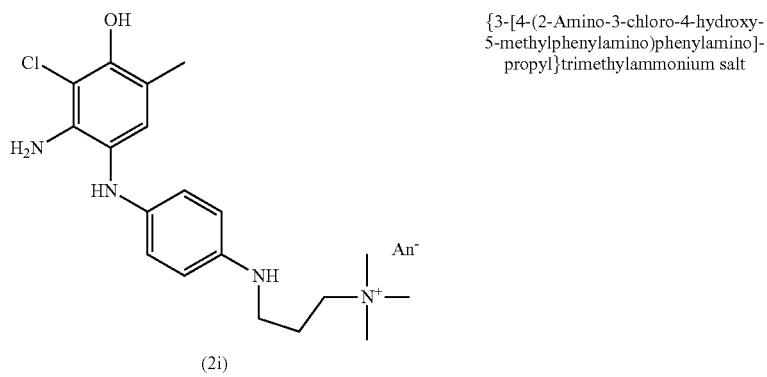
{3-[4-(2-Amino-3-chloro-4-hydroxy-5-methylphenylamino)phenylamino]-propyl}trimethylammonium salt
(2i)
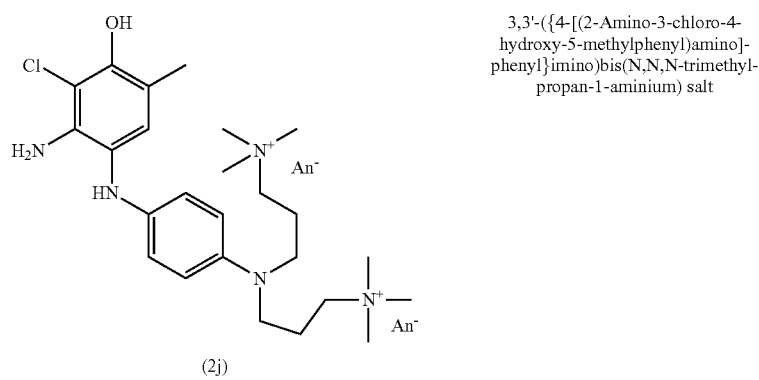
3,3'-({4-[(2-Amino-3-chloro-4-hydroxy-5-methylphenyl)amino]-phenyl}imino)bis(N,N,N-trimethyl-propan-1-aminium) salt
(2j)
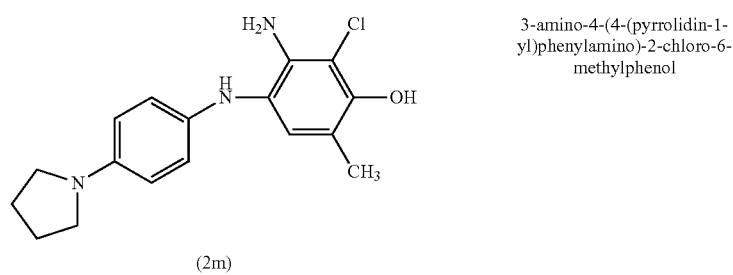
3-amino-4-(4-(pyrrolidin-1-yl)phenylamino)-2-chloro-6-methylphenol
(2m)

-continued

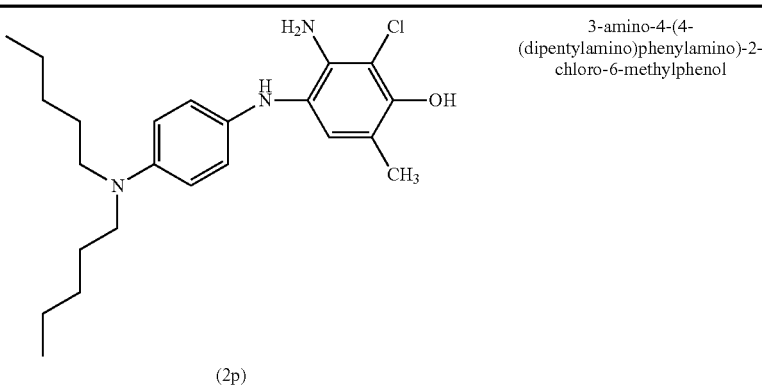

3-amino-4-(4-(dipentylamino)phenylamino)-2-chloro-6-methylphenol (2p)

with An⁻, which are identical or different, representing an anionic counterion, such as halide; particularly, An⁻ represents a chloride.

More particularly, the dyes present in the composition are chosen from the preceding dyes (1a), (1b), (1c), (1d), (1e), (1f), (1g) and (1i) and their organic or inorganic acid salts, their geometrical isomers, their tautomers and their solvates, such as hydrates. According to another specific form of the invention, the preferred compounds are the compounds (1m) and (1p).

The compounds of formula (I) or (II) of the invention are prepared according to the following general synthetic routes:

1—Access to the Compounds Corresponding to the Formula (I):

The compounds corresponding to the formula (I) are obtained in the general way by reacting 2-chloro-3-amino-6-methylphenol derivatives with a para-aminophenol derivative (X=OH) or a para-phenylenediamine derivative (X=NR$_4$R$_5$), preferably in a basic medium, in the presence of an oxidizing agent. The base used is preferably an aqueous ammonia or sodium hydroxide solution and the oxidizing agent is preferably chosen from aqueous hydrogen peroxide solution, potassium ferricyanide, air, ammonium persulphate and manganese oxide.

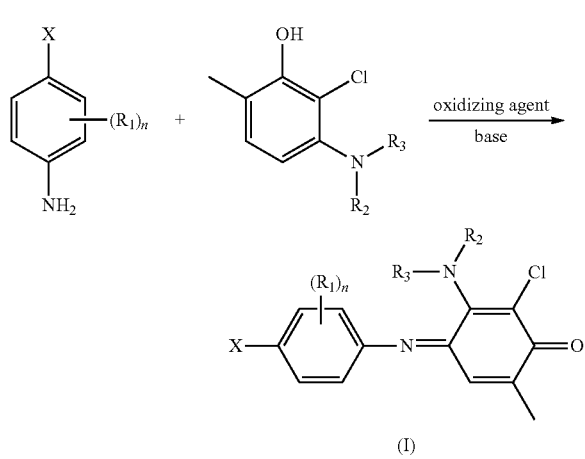

Similar synthetic approaches are described in Patents FR 2 234 277, FR 2 047 932, FR 2 106 661 and FR 2 121 101.

2—Access to the Compounds Corresponding to the Formula (II):

The compounds corresponding to the formula (II) are obtained in a general way by reacting the compounds of formula (I) with a reducing agent. This preferred reducing agent is sodium hydrosulphite.

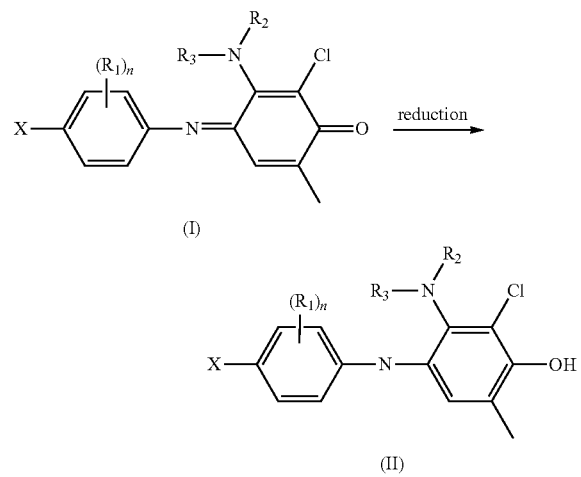

Similar synthetic approaches are described in Patents FR 2 056 799, FR 2 047 932, FR 2 165 965 and FR 2 262 023.

Another subject-matter of the invention relates to a dyeing composition for dyeing keratinous fibres, in particular human keratinous fibres, such as the hair, comprising, in a cosmetic medium, direct dyes of formula (I) or dyeing precursors of formula (II).

The dyeing composition of use in the invention generally comprises an amount of dye of formula (I) or of precursor of formula (II) of between 0.001 and 30% by weight, with respect to the total weight of the composition. Preferably, this amount is between 0.005 and 10% by weight and more preferably still between 0.01 and 6% by weight, with respect to the total weight of the composition.

The dyeing composition comprising the dye of formula (I) or, preferably, the precursor of formula (II) can also comprise an oxidizing agent, such as hydrogen peroxide, urea hydrogen peroxide, alkali metal bromates, persalts, peracids and oxidase enzymes.

The dyeing composition can additionally comprise additional direct dyes other than those of formula (I) or (II). These direct dyes are, for example, chosen from neutral, acid or cationic nitrobenzene direct dyes, neutral, acid or cationic azo direct dyes, tetraazapentamethine dyes, neutral, acid or cationic quinone and in particular anthraquinone dyes, azine direct dyes, triarylmethane direct dyes, indoamine direct dyes and natural direct dyes.

Mention may be made, among nitrobenzene direct dyes, without implying limitation, of the following compounds:

1,4-Diamino-2-nitrobenzene, 1-amino-2-nitro-4-(β-hydroxyethylamino)benzene, 1-amino-2-nitro-4-[bis(β-hydroxyethyl)amino]benzene, 1,4-bis(β-hydroxyethylamino)-2-nitrobenzene, 1-(β-hydroxyethylamino)-2-nitro-4-[bis(β-hydroxyethyl)amino]benzene, 1-(β-hydroxyethylamino)-2-nitro-4-aminobenzene, 1-(β-hydroxyethylamino)-2-nitro-4-[(ethyl)(β-hydroxyethyl)amino]benzene, 1-amino-3-methyl-4-(β-hydroxyethylamino)-6-nitrobenzene, 1-amino-2-nitro-4-(β-hydroxyethylamino)-5-chlorobenzene, 1,2-diamino-4-nitrobenzene, 1-amino-2-(β-hydroxyethylamino)-5-nitrobenzene, 1,2-bis(β-hydroxyethylamino)-4-nitrobenzene, 1-amino-2-[tris(hydroxymethyl)methylamino]-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-(β-hydroxyethyloxy)-2-(β-hydroxyethylamino)-5-nitrobenzene, 1-methoxy-2-(β-hydroxyethylamino)-5-nitrobenzene, 1-(β-hydroxyethyloxy-3-methylamino)-4-nitrobenzene, 1-(β,γ-dihydroxypropyloxy)-3-methylamino-4-nitrobenzene, 1-((3-hydroxyethylamino)-4-(β,γ-dihydroxypropyloxy)-2-nitrobenzene, 1-(β,γ-dihydroxypropylamino)-4-trifluoromethyl-2-nitrobenzene, 1-(β-hydroxyethylamino)-4-trifluoromethyl-2-nitrobenzene, 1-(β-hydroxyethylamino)-3-methyl-2-nitrobenzene, 1-(β-aminoethylamino)-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-[bis(β-hydroxyethyl)amino]-3-nitrobenzene, 1-(β-hydroxyethylamino)-2-nitrobenzene or 1-hydroxy-4-(β-hydroxyethylamino)-3-nitrobenzene.

Mention may be made, among azo direct dyes, of the cationic azo dyes described in Patent Applications WO 95/15144, WO-95/01772 and EP-714 954, the contents of which form an integral part of the invention.

Mention may very particularly be made, among these compounds, of the following dyes: 1,3-dimethyl-2-[[4-(dimethylamino)phenyl]azo]-1H-imidazolium chloride, 1,3-dimethyl-2-[(4-aminophenyl)azo]-1H-imidazolium chloride or 1-methyl-4-[(methylphenylhydrazono)methyl]-pyridinium methyl sulphate.

Mention may also be made, among azo direct dyes, of the following dyes, described in the Colour Index International, 3rd edition:

Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24 and Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Mention may be made, among quinone direct dyes, of the following dyes:

Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15 and Basic Blue 99, and also the following compounds: 1-(N-methyl-morpholiniopropylamino)-4-hydroxyanthraquinone, 1-aminopropylamino-4-methylaminoanthraquinone, 1-aminopropylaminoanthraquinone, 5-(β-hydroxyethyl)-1,4-diaminoanthraquinone, 2-aminoethylaminoanthraquinone and 1,4-bis(β,γ-dihydroxypropylamino)anthraquinone.

Mention may be made, among azine dyes, of the following compounds:

Basic Blue 17 and Basic Red 2.

Mention may be made, among triarylmethane dyes, of the following compounds: Basic Green 1, Acid Blue 9, Basic Violet 3, Basic Violet 14, Basic Blue 7, Acid Violet 49, Basic Blue 26 and Acid Blue 7.

Mention may be made, among indoamine dyes, of the following compounds:

2-(β-hydroxyethylamino-5-[bis(β-4'-hydroxyethyl)amino]anilino-1,4-benzoquinone;

2-(β-hydroxyethylamino-5-(2'-methoxy-4'-aminoanilino)-1,4-benzoquinone;

3-N-(2'-chloro-4'-hydroxy)phenylacetylamino-6-methoxy-1,4-benzoquinone imine;

3-N-(3'-chloro-4'-methylamino)phenylureido-6-methyl-1,4-benzoquinone imine;

3-[4'-N-(ethyl,carbamylmethyl)-amino]phenylureido-6-methyl-1,4-benzoquinone imine.

Mention may be made, among natural direct dyes, of lawsone, juglone, alizarin, purpurin, carminic acid, kermesic acid, purpurogallin, protocatechualdehyde, indigo, isatin, curcumin, spinulosin or apigenidine. It is also possible to use extracts or decoctions comprising these natural dyes and in particular cataplasms or henna-based extracts.

The dyeing composition can comprise one or more oxidation bases and/or one or more couplers conventionally used for the dyeing of keratinous fibres.

Mention may be made, among oxidation bases, of para-phenylenediamines, bisphenylalkylenediamines, para-aminophenols, bis-para-aminophenols, ortho-aminophenols, heterocyclic bases and their addition salts.

Mention may in particular be made, among couplers, of meta-phenylenediamines, meta-aminophenols, meta-diphenols, naphthalene couplers, heterocyclic couplers and their addition salts.

The coupler or couplers are each generally present in an amount of between 0.001 and 10% by weight of the total weight of the dyeing composition, preferably between 0.005 and 6% by weight.

The oxidation base or bases present in the dyeing composition are generally present each in an amount of between 0.001 and 10% by weight of the total weight of the dyeing composition, preferably between 0.005 and 6% by weight.

Generally, the addition salts of the oxidation bases and couplers which can be used in the context of the invention are chosen in particular from the addition salts with an acid, such as hydrochlorides, hydrobromides, sulphates, citrates, succinates, tartrates, lactates, tosylates, benzenesulphonates, phosphates and acetates, and the addition salts with a base, such as alkali metal hydroxides, such as sodium hydroxide or potassium hydroxide, ammonia, amines or alkanolamines.

The medium appropriate for the dyeing, also known as dyeing vehicle, is a cosmetic medium generally comprising water or a mixture of water and of at least one organic solvent. Mention may be made, as organic solvent, for example, of lower $C_1$-$C_4$ alkanols, such as ethanol and isopropanol, polyols and polyol ethers, such as 2-butoxyethanol, propylene glycol, propylene glycol monomethyl ether, diethylene glycol monoethyl ether and diethylene glycol monomethyl ether, aromatic alcohols, such as benzyl alcohol or phenoxyethanol, and their mixtures.

The solvents, when they are present, are preferably present in proportions preferably of between 1 and 50% by weight approximately, with respect to the total weight of the dyeing composition, more preferably still between 5 and 40% by weight approximately.

The dyeing composition can also include various adjuvants conventionally used in hair dyeing compositions, such as anionic, cationic, nonionic, amphoteric or zwitterionic surface-active agents or their mixtures, anionic, cationic or nonionic, amphoteric or zwitterionic polymers or their mixtures, inorganic or organic thickening agents, in particular anionic, cationic, nonionic and amphoteric polymeric associative thickeners, antioxidants, penetrating agents, sequestering agents, fragrances, buffers, dispersing agents, conditioning agents, such as, for example, volatile or non-volatile and modified or unmodified silicones, such as animated silicones, film-forming agents, ceramides, preservatives, opacifying agents or conducting polymers.

The above adjuvants are generally present in an amount of, for each of them, between 0.01 and 20% by weight, with respect to the weight of the composition.

Of course, a person skilled in the art will take care to choose this or these optional additional compounds so that the advantageous properties intrinsically attached to the dyeing composition in accordance with the invention are not, or not substantially, detrimentally affected by the envisaged addition or additions.

The pH of the dyeing composition is generally between 3 and 14 approximately. It can be adjusted to the desired value using acidifying or basifying agents commonly used in dyeing keratinous fibres or else using conventional buffer systems.

According to a specific form of the invention, when the dyeing composition comprises at least one dye of formula (I), the composition has a pH of between 6 and 11. According to another specific form of the invention, when the composition comprises at least one dyeing precursor of formula (II), the composition has a pH of between 6 and 11.

Mention may be made, among acidifying agents, by way of example, of inorganic or organic acids, such as hydrochloric acid, orthophosphoric acid, sulphuric acid, carboxylic acids, such as acetic acid, tartaric acid, citric acid or lactic acid, or sulphonic acids.

Mention may be made, among basifying agents, by way of example, of ammonia, alkaline carbonates, alkanolamines, such as mono-, di- and triethanolamines and their derivatives, sodium hydroxide, potassium hydroxide and the compounds of following formula (γ):

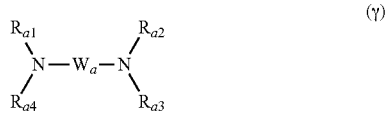

in which $W_a$ is a propylene residue optionally substituted by a hydroxyl group or a $C_1$-$C_4$ alkyl radical and $R_{a1}$, $R_{a2}$, $R_{a3}$ and $R_{a4}$, which are identical or different, represent a hydrogen atom, a $C_1$-$C_4$ alkyl radical or a $C_1$-$C_4$ hydroxyalkyl radical.

The dyeing composition can be provided in various forms, such as in the liquid, cream or gel form or in any other form appropriate for carrying out dyeing of keratinous fibres and in particular the hair.

Another subject-matter of the invention is a method for dyeing keratinous fibres, in particular the hair, which consists in applying, to the keratinous substances, in the presence or absence of an oxidizing agent, a dyeing composition comprising, in a cosmetic medium, at least one azomethine dye of formula (I) or a dyeing precursor of formula (II) as defined above.

After a leave-in time, the keratinous fibres are rinsed, leaving coloured fibres to appear. The leave-in time is generally between 3 and 50 minutes approximately, preferably from 5 to 40 minutes approximately.

The application of the dyeing composition according to the invention is generally carried out at ambient temperature. However, it can be carried out at temperatures varying from 20 to 80° C.

The examples which follow serve to illustrate the invention without, however, exhibiting a limiting nature. The dyes of the examples below were fully characterized by conventional spectroscopic and spectrometric methods.

EXAMPLES

Synthetic Examples

Example 1

Synthesis of 3-amino-2-chloro-4-(4-hydroxyphenylimino)-6-methylcyclohexa-2,5-dienone 1 (Compound (1a))

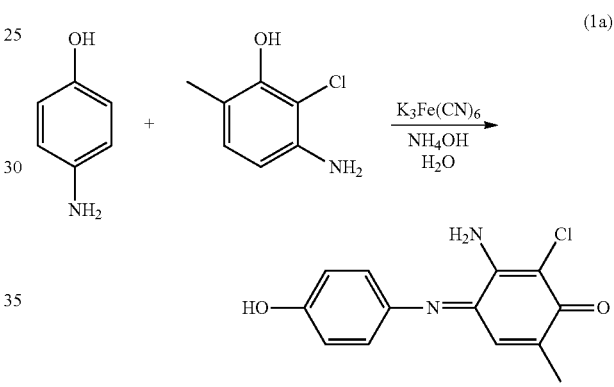

9.7 g (0.05 mol) of 3-amino-2-chloro-6-methylphenol, dissolved in 250 ml of water, are added to a solution comprising 5.45 g (0.05 mol) of para-aminophenol, 150 ml of water and 80 ml of 20% ammonium hydroxide in water in a conical flask.

A solution of 32.9 g (0.1 mol) of potassium ferricyanide dissolved in 150 ml of water is subsequently added and the reaction medium is stirred at ambient temperature for 2 hours.

The solid formed is filtered off, washed with water and then recrystallized from an ethanol/water 75/25 mixture. 4.4 g of 3-amino-2-chloro-4-(4-hydroxyphenylimino)-6-methylcyclohexa-2,5-dienone of formula (1a) are obtained.

Example 2

Synthesis of 3-amino-4-(4-aminophenylimino)-2-chloro-6-methylcyclohexa-2,5-dienone 2 (Compound (1b))

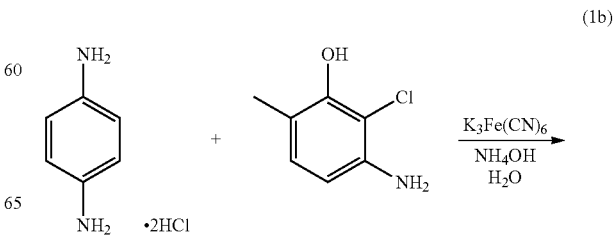

-continued

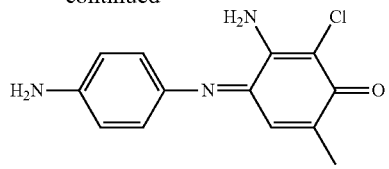

A solution of 9 g (0.05 mol) of para-phenylenediamine dihydrochloride in 250 ml of water is mixed in a conical flask with a solution of 9.7 g (0.05 mol) of 3-amino-2-chloro-6-methylphenol in 250 ml of water and 80 ml of a 20% aqueous ammonium hydroxide solution. 32.9 g (0.1 mol) of potassium ferricyanide are subsequently added portionwise and the reaction medium is diluted with 150 ml of water. After stirring at ambient temperature for 12 hours, the solid formed is filtered off and then washed with water.

The crude resulting product is subsequently purified by chromatography on a silica column (eluent: dichloromethane-dichloromethane/methanol: 90/10).

2.1 g of 3-amino-4-(4-aminophenylimino)-2-chloro-6-methylcyclohexa-2,5-dienone of formula (1b) are obtained.

Example 3

Synthesis of 3-amino-4-(4-amino-methylphenylimino)-2-chloro-6-methylcyclohexa-2,5-dienone 3 (Compound of Formula (1c))

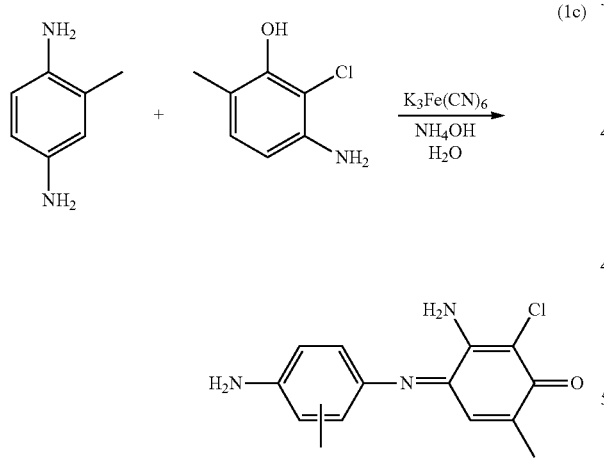

9.7 g (0.05 mol) of 3-amino-2-chloro-6-methylphenol, dissolved in 250 ml of water, are added to a solution comprising 9.75 g (0.05 mol) of para-toluenediamine, 250 ml of water and 40 ml of 20% ammonium hydroxide in water in a conical flask.

A solution of 32.9 g (0.1 mol) of potassium ferricyanide dissolved in 150 ml of water is subsequently added and the reaction medium is stirred at ambient temperature for 3 h 20.

The solid formed is filtered off, washed with water and then purified by chromatography on a silica column (eluent: dichloromethane/methanol: 99/1). 2.98 g of 3-amino-4-(4-amino-methylphenylimino)-2-chloro-6-methylcyclohexa-2,5 dienone of formula (1c) are obtained.

Example 4

Synthesis of 3-amino-4-[(4-aminophenyl)amino]-2-chloro-6-methylphenol (2b)

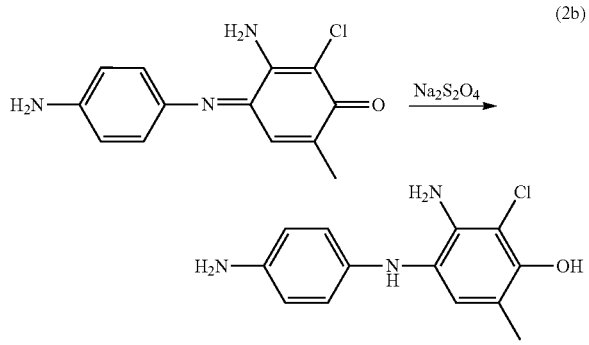

10 mg (0.04 mol) of (4Z)-3-amino-4-[(4-aminophenyl)imino]-2-chloro-6-methylcyclohexa-2,5-dien-1-one are added to a solution comprising 16 mg of sodium hydrosulphite in 500 µl of methanol and 5 µl of an aqueous sodium hydroxide solution. The reaction medium is stirred and then the solution is treated according to the usual procedure and characterized. 3-Amino-4-[(4-aminophenyl)amino]-2-chloro-6-methylphenol) (2b) is obtained.

Example 5

Synthesis of 3-amino-4-[(4-amino-2-methylphenyl)amino]-2-chloro-6-methylphenol/3-amino-4-[(4-amino-3-methylphenyl)amino]-2-chloro-6-methylphenol (2c)

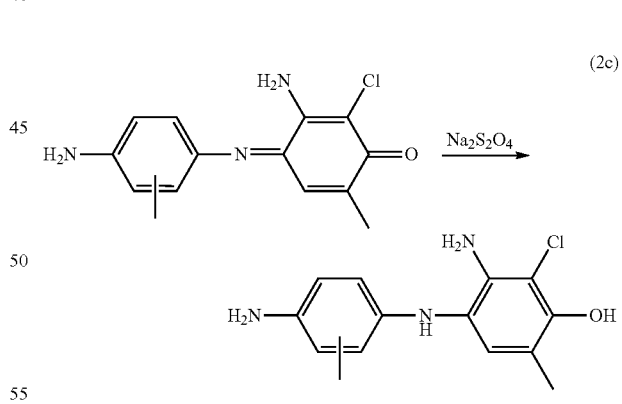

10 mg (0.04 mol) of 3-amino-4-[(4-amino-2-methylphenyl)imino]-2-chloro-6-methylcyclohexa-2,5-dien-1-one and 3-amino-4-[(4-amino-3-methylphenyl)imino]-2-chloro-6-methylcyclohexa-2,5-dien-1-one are added to a solution comprising 16 mg of sodium hydrosulphite in 500 µl of methanol and 5 µl of an aqueous sodium hydroxide solution. The reaction medium is stirred and then the solution is treated according to the usual procedure and characterized. 3-Amino-4-[(4-amino-2-methylphenyl)amino]-2-chloro-6-methylphenol/3-amino-4-[(4-amino-3-methylphenyl)amino]-2-chloro-6-methylphenol (2c) are obtained.

Example 6

Synthesis of 3-amino-2-chloro-4-[(4-hydroxyphenyl)amino]-6-methylphenol (2a)

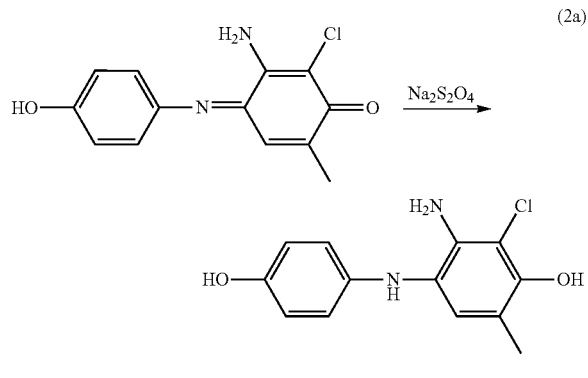

10 mg (0.04 mol) of 3-amino-2-chloro-4-[(4-hydroxyphenyl)imino]-6-methylcyclohexa-2,5-dien-1-one are added to a solution comprising 16 mg of sodium hydrosulphite in 500 µl of methanol and 5 µl of an aqueous sodium hydroxide solution. The reaction medium is stirred and then the solution is treated according to the usual procedure and characterized. 3-Amino-2-chloro-4-[(4-hydroxyphenyl)amino]-6-methylphenol (2a) is obtained.

Example 7

Synthesis of 3-amino-2-chloro-4-({4-[ethyl(2-hydroxyethyl)amino]phenyl}imino)-6-methylcyclohexa-2,5-dien-1-one (1k)

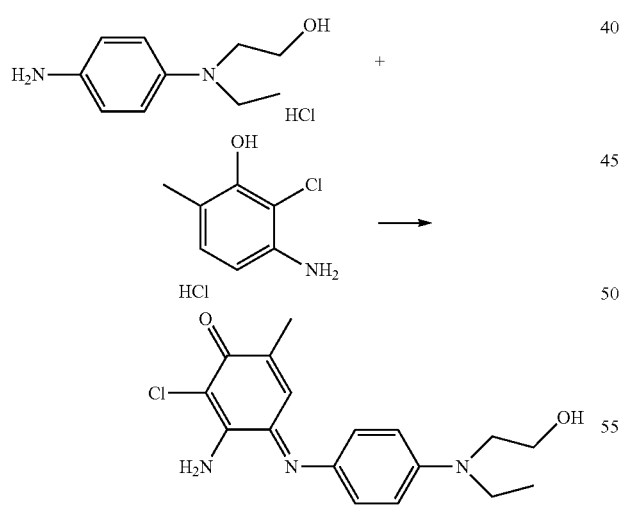

1.94 g of 3-amino-2-chloro-6-methylphenol hydrochloride are added to 2.53 g of 2-[(4-aminophenyl)(ethyl)amino]ethanol hydrochloride in solution in 20 ml of water and 10 ml of ethanol. The pH is adjusted to 9.5 with 20% ammonium hydroxide in water. 36 ml of 9% aqueous hydrogen peroxide solution are subsequently added and the reaction medium is stirred at ambient temperature for 4 h 30. The solid form is filtered off and washed with water; 2.44 g of 3-amino-2-chloro-4-({4-[ethyl(2-hydroxyethyl)amino]phenyl}imino)-6-methylcyclohexa-2,5-dien-1-one (1k) are obtained.

Example 8

Synthesis of 3-amino-2-chloro-4-{[4-(3-hydroxypyrrolidin-1-yl)phenyl]imino}-6-methylcyclohexa-2,5-dien-1-one (1l)

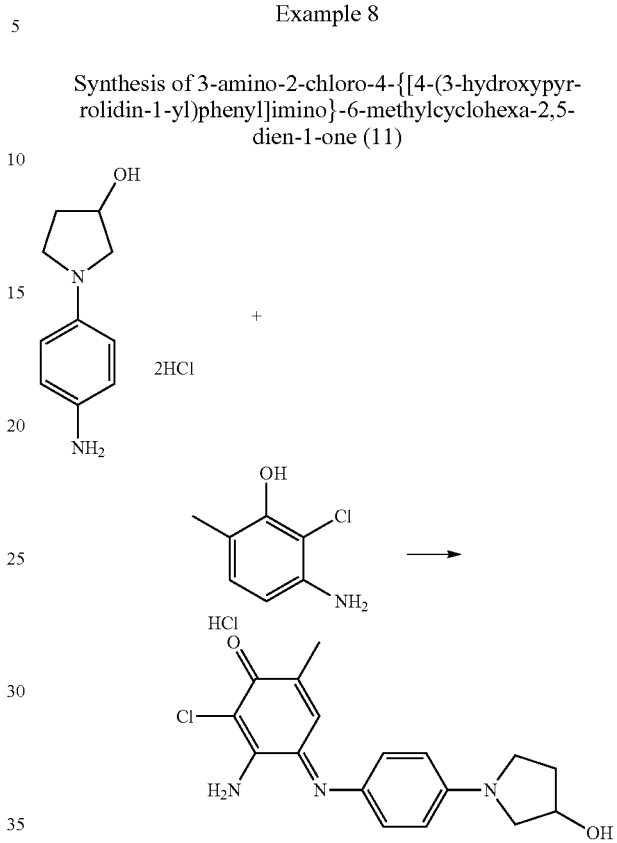

1.94 g of 3-amino-2-chloro-6-methylphenol hydrochloride are added to 2.51 g of 1-(4-aminophenyl)pyrrolidin-3-ol dihydrochloride in solution in 20 ml of water and 20 ml of ethanol. The pH is adjusted to 9.5 with 20% ammonium hydroxide and then 18 ml of 9% aqueous hydrogen peroxide solution are added. The mixture is left stirring at ambient temperature for 8 hours and then the precipitate formed is filtered off. 2.79 g of 3-amino-2-chloro-4-{[4-(3-hydroxypyrrolidin-1-yl)phenyl]imino}-6-methylcyclohexa-2,5-dien-1-one (1l) are thus obtained.

Example 9

Synthesis of 3-amino-2-chloro-6-methyl-4-[(4-pyrrolidin-1-ylphenyl)imino]cyclohexa-2,5-dien-1-one (1m)

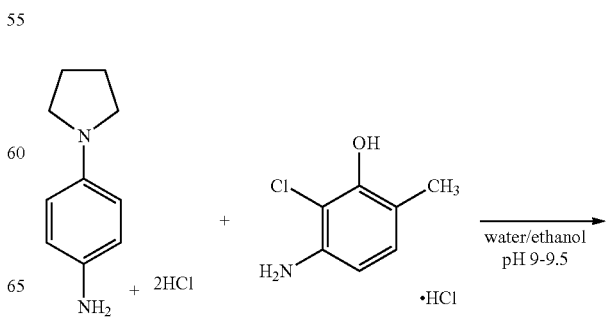

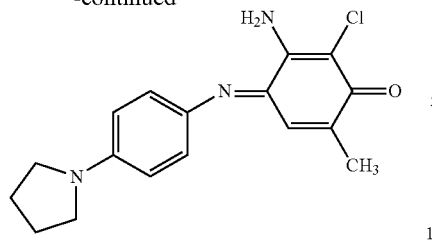

1.94 g of 3-amino-2-chloro-6-methylphenol hydrochloride are added to 2.35 g of 4-(pyrrolidin-1-yl)aniline dihydrochloride in solution in 15 ml of water and 15 ml of ethanol. The pH is adjusted to 9.5 with 20% ammonium hydroxide and then 18 ml of 9% aqueous hydrogen peroxide solution are added. The mixture is left stirring at ambient temperature for 4 hours and then the precipitate formed is filtered off. 1.7 g of 3-amino-2-chloro-6-methyl-4-[(4-pyrrolidin-1-ylphenyl)imino]cyclohexa-2,5-dien-1-one (1m) are thus obtained.

Example 10

Synthesis of 3-amino-2-chloro-6-methyl-4-{[4-(methylamino)phenyl]imino}cyclohexa-2,5-dien-1-one (1n)

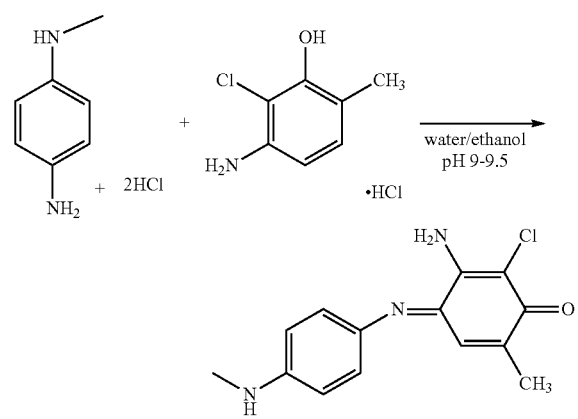

A mixture of 2 g of N-methylbenzene-1,4-diamine dihydrochloride, 2 g of 3-amino-2-chloro-6-methylphenol hydrochloride, 20 ml of water, 20 ml of ethanol and 7.6 ml of 9% aqueous hydrogen peroxide solution, a mixture brought to pH 9.5 with 20% ammonium hydroxide in water, is stirred at ambient temperature for 5 hours. 2.5 g of 3-amino-2-chloro-6-methyl-4-{[4-(methylamino)phenyl]imino}cyclohexa-2,5-dien-1-one (1n) are obtained.

Example 11

Synthesis of 3-amino-2-chloro-4-{[4-(dipentylamino)phenyl]imino}-6-methylcyclohexa-2,5-dien-1-one (1o)

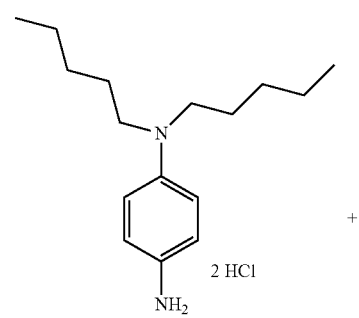

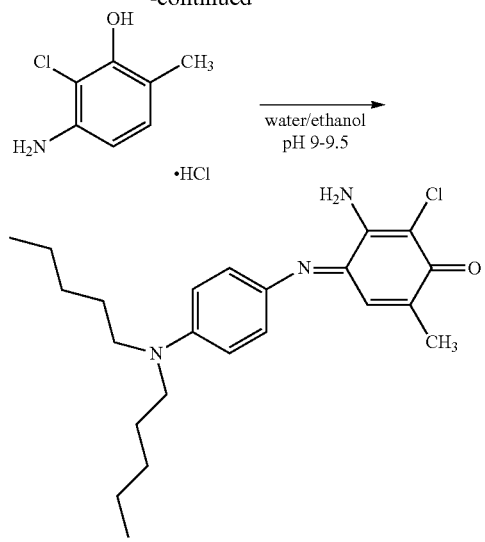

0.48 g of 3-amino-2-chloro-6-methylphenol hydrochloride is added to 0.8 g of N,N-dipentylbenzene-1,4-diamine dihydrochloride in solution in 5 ml of water and 40 ml of ethanol. The pH is adjusted to 9.5 with 20% ammonium hydroxide and then 1.7 ml of 9% aqueous hydrogen peroxide solution are added. The mixture is left stirring at ambient temperature for 5 hours and then the precipitate formed is filtered off. 0.72 g of 3-amino-2-chloro-4-{[4-(dipentylamino)phenyl]imino}-6-methylcyclohexa-2,5-dien-1-one (1o) is thus obtained.

Example 12

Synthesis of 3-amino-4-({4-[bis(2-hydroxyethyl)amino]phenyl}imino)-2-chloro-6-methylcyclohexa-2,5-dien-1-one (1p)

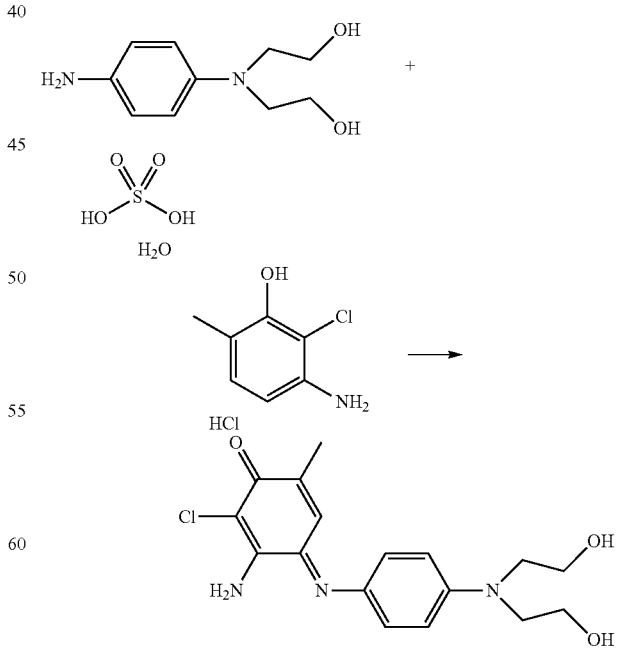

1.69 g of 3-amino-2-chloro-6-methylphenol hydrochloride are added to 2.715 g of 2,2'-[(4-aminophenyl)imino]diethanol sulphate in solution in 32 ml of water and 32 ml of ethanol. The pH is adjusted to 9.5 with 20% ammonium hydroxide and then 31.5 ml of 9% aqueous hydrogen peroxide solution are added. The mixtures is left stirring at ambient temperature for 6 hours and then the precipitate formed is filtered off.

1.68 g of 3-amino-4-({4-[bis(2-hydroxyethyl)amino] phenyl}imino)-2-chloro-6-methylcyclohexa-2,5-dien-1-one (1p) are thus obtained.

Example 13

Synthesis of the mixture of 3-amino-4-[(4-amino-2-methylphenyl)imino]-2-chloro-6-methylcyclohexa-2, 5-dien-1-one and 3-amino-4-[(4-amino-3-methyl-phenyl)imino]-2-chloro-6-methylcyclohexa-2,5-dien-1-one Isomers (1q)

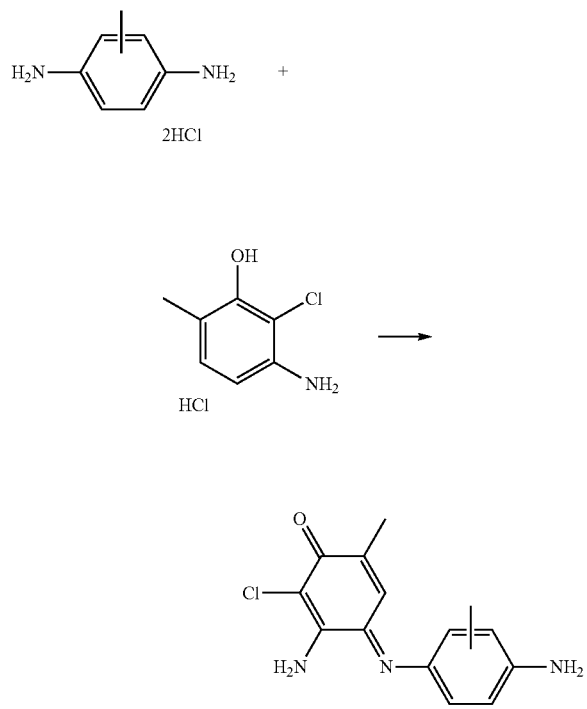

9.7 g (0.05 mol) of 3-amino-2-chloro-6-methylphenol, dissolved in 250 ml of water, are added to a solution comprising 9.75 g (0.05 mol) of 2-methylbenzene-1,4-diamine dihydrochloride, 250 ml of water and 40 ml of 20% ammonium hydroxide in water in a conical flask.

A solution of 32.9 g (0.1 mol) of potassium ferricyanide dissolved in 150 ml of water is subsequently added dropwise and the reaction medium is stirred at ambient temperature for 2 hours.

The solid formed is filtered off, washed with water, dried and then purified by silica chromatography (eluent:dichloromethane 99/methanol 1). 2.98 g of the mixture of 3-amino-4-[(4-amino-2-methylphenyl)imino]-2-chloro-6-methylcyclohexa-2,5-dien-1-one and (3-amino-4-[(4-amino-3-methylphenyl)imino]-2-chloro-6-methylcyclohexa-2,5-dien-1-one isomers (1q) are thus obtained.

Example 14

Synthesis of 1-[1-(4-{[2-amino-3-chloro-5-methyl-4-oxocyclohexa-2,5-dien-1-ylidene]amino}phenyl) pyrrolidin-3-yl]-3-methyl-1H-imidazol-3-ium chloride (1r)

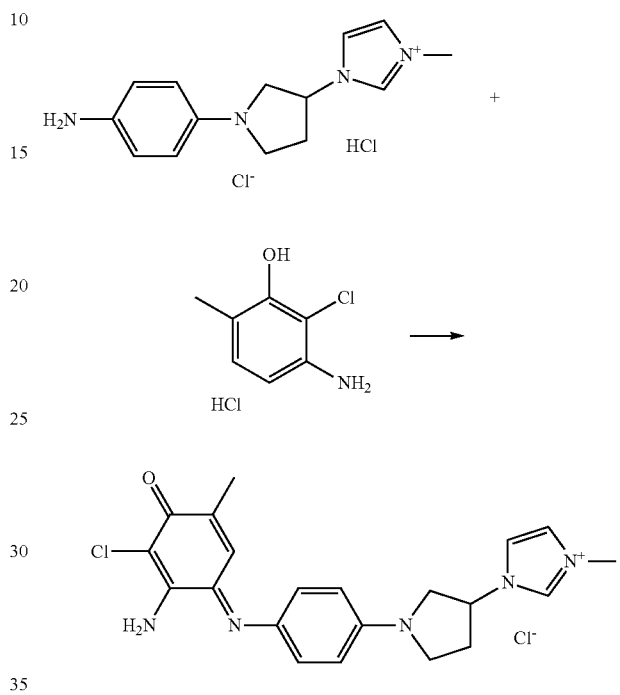

315 mg of 1-[1-(4-aminophenyl)pyrrolidin-3-yl]-3-methyl-1H-imidazol-3-ium chloride hydrochloride and 194.1 mg of 3-amino-2-chloro-6-methylphenol hydrochloride are weighed out in a flask, 1 ml of water is added and the pH is adjusted to 9.5 with 20% ammonium hydroxide in water.

0.5 ml of 30% aqueous hydrogen peroxide solution is added dropwise. The reaction is exothermic and the temperature rises to 60° C.

The mixture is left stirring for 18 hours. The precipitate is filtered off and rinsed with acetone. The next morning, a second precipitate has formed in the filtrate and is filtered off. 81 mg of 1-[1-(4-{[2-amino-3-chloro-5-methyl-4-oxocyclohexa-2,5-dien-1-ylidene]amino}phenyl)pyrrolidin-3-yl]-3-methyl-1H-imidazol-3-ium chloride (1r) are thus obtained.

Example 15

Synthesis of 1-(4-{[2-amino-3-chloro-5-methyl-4-oxocyclohexa-2,5-dien-1-ylidene]amino}phenyl)-N,N,N-trimethylpyrrolidin-3-aminium chloride (1t)

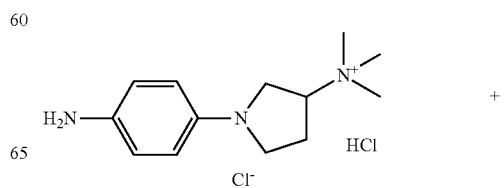

-continued

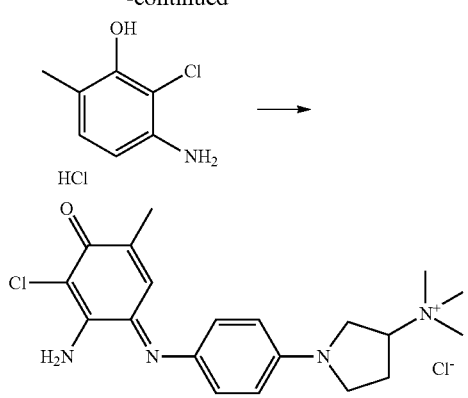

292.5 mg of 1-(4-aminophenyl)-N,N,N-trimethylpyrrolidin-3-aminium chloride hydrochloride and 194.1 mg of 3-amino-2-chloro-6-methylphenol hydrochloride are weighed out in a flask, 1 ml of water is added and the pH is adjusted to 9.5 with 20% ammonium hydroxide in water. 1.1 ml of 30% aqueous hydrogen peroxide solution are added dropwise. The mixture is left stirring for 24 hours. The precipitate is filtered off and rinsed with acetone. 80 mg of 1-(4-{[2-amino-3-chloro-5-methyl-4-oxocyclohexa-2,5-dien-1-ylidene]amino}phenyl)-N,N,N-trimethylpyrrolidin-3-aminium chloride (1t) are thus obtained.

Dyeing Examples

Dyeing in a Neutral Medium

The following dyeing compositions (A) and (B) are prepared from the dyes compound (1b) and compound (1c) synthesized above.

|  | Composition | |
|---|---|---|
|  | (A) | (B) |
| Compound (1b) | $10^{-3}$ mol | — |
| Compound (1c) | — | $10^{-3}$ mol |
| Dyeing vehicle (1) | (*) | (*) |
| Demineralized water q.s. for | 100 g | 100 g |

(*): Dyeing vehicle (1) pH = 7 with the dyeing vehicle composed of:
| 96° Ethyl alcohol | 20.8 g |
| Pentasodium salt of diethylenetriaminepentaacetic acid as a 40% aqueous solution | 0.48 g A.M |
| $C_8$-$C_{10}$ alkyl polyglucoside as a 60% aqueous solution | 3.6 g A.M |
| Benzyl alcohol | 2.0 g |
| Polyethylene glycol comprising 8 ethylene oxide units | 3.0 g |
| $Na_2HPO_4$ | 0.28 g |
| $KH_2PO_4$ | 0.46 g |

Compositions (A) and (B) are applied to locks of white hair comprising 90% of white hairs. After a leave-in time of 30 minutes, the locks are rinsed, washed with a standard shampoo, rinsed again and then dried.

The shades obtained appear in the table below:

|  | Composition | |
|---|---|---|
|  | (A) | (B) |
| Shade observed after treatment | Purple red | Vivid purple |

Dyeing in a Basic Medium

The following dyeing compositions (C) to (E) are prepared from compounds (1a) to (1c) respectively.

|  | Composition | | |
|---|---|---|---|
|  | (C) | (D) | (E) |
| Compound (1a) | $10^{-3}$ mol | — | — |
| Compound (1b) | — | $10^{-3}$ mol | — |
| Compound (1c) | — | — | $10^{-3}$ mol |
| Dyeing vehicle (2) | (*) | (*) | (*) |
| Demineralized water q.s. for | 100 g | 100 g | 100 g |

(*): Dyeing vehicle (2) pH = 9.5 with the dyeing vehicle composed of:
| 96° Ethyl alcohol | 20.8 g |
| Pentasodium salt of diethylenetriaminepentaacetic acid as a 40% aqueous solution | 0.48 g A.M |
| $C_8$-$C_{10}$ alkyl polyglucoside as a 60% aqueous solution | 3.6 g A.M |
| Benzyl alcohol | 2.0 g |
| Polyethylene glycol comprising 8 ethylene oxide units | 3.0 g |
| $NH_4Cl$ | 4.32 g |
| Aqueous ammonia comprising 20% of $NH_3$ | 2.94 g |

Compositions (C) to (E) are applied to locks of white hair comprising 90% of white hairs. After a leave-in time of 30 minutes, the locks are rinsed, washed with a standard shampoo, rinsed again and then dried.

The shades obtained appear in the table below:

|  | Composition | | |
|---|---|---|---|
|  | (C) | (D) | (E) |
| Shade observed after treatment | Light orangey | Crimson | Purple |

The invention claimed is:

1. At least one entity chosen from compounds of formula (I) and compounds of formula (II):

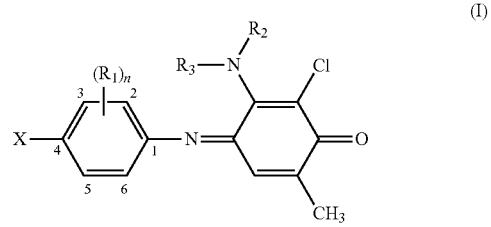

-continued

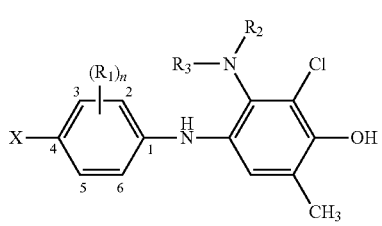
(II)

organic salts, inorganic salts, geometrical isomers, tautomers, and solvates thereof, wherein in formula (I) or formula (II):

$R_1$ is independently chosen from:
- chlorine;
- $C_1$-$C_3$ alkyl radical optionally substituted by at least one hydroxyl group; and
- $C_1$-$C_3$ alkoxy radical optionally substituted by at least one hydroxyl group;

X is independently chosen from:
- hydroxyl;
- $NR_4R_5$ radicals wherein $R_4$ and $R_5$ are each independently chosen from
  - i) hydrogen; and
  - ii) a $C_1$-$C_5$ alkyl radical optionally substituted by at least one group chosen from hydroxyl, $C_1$-$C_3$ alkoxy, amino, $C_1$-$C_3$ alkylamino, di($C_1$-$C_3$) alkylamino, aminocarbonyl, —COOH, —SO$_3$H, tri($C_1$-$C_3$)alkylammonium, and $C_1$-$C_3$ alkylimidazolium;
- pyrrolidinyl radical optionally substituted by at least one group chosen from hydroxyl, $C_1$-$C_3$ alkoxy, amino, $C_1$-$C_3$ alkylamino, di($C_1$-$C_3$) alkylamino, tri($C_1$-$C_3$) alkylammonium, and $C_1$-$C_3$ alkylimidazolium;
- a piperidinyl radical optionally substituted by at least one group chosen from hydroxyl, $C_1$-$C_3$ alkoxy, amino, $C_1$-$C_3$ alkylamino, di($C_1$-$C_3$) alkylamino, tri($C_1$-$C_3$)alkylammonium, and $C_1$-$C_3$ alkylimidazolium;

n is an integer chosen from 0, 1, 2, and 3;

$R_2$ and $R_3$ are independently chosen from:
- i) hydrogen; and
- ii) a $C_1$-$C_5$ alkyl radical optionally substituted by at least one group chosen from hydroxyl, $C_1$-$C_3$ alkoxy, amino, $C_1$-$C_3$ alkylamino, di($C_1$-$C_3$) alkylamino, aminocarbonyl, —COOH, —SO$_3$H, tri($C_1$-$C_3$)alkylammonium, and $C_1$-$C_3$ alkylimidazolium;

wherein at least one of X, $R_2$, $R_2$, $R_3$, $R_4$, and $R_5$ comprise a cationic group, the electrical neutrality of at least one entity is achieved by at least one cosmetically acceptable anionic counterion.

2. The at least one entity according to claim 1, wherein n is 1 and $R_1$ is chosen from $C_1$-$C_3$ alkyl radicals.

3. The at least one entity according to claim 1, wherein n is 0.

4. The at least one entity according to claim 1, wherein X is hydroxyl.

5. The at least one entity according to claim 1, wherein X is chosen from $NR_4R_5$ radicals wherein $R_4$ and $R_5$ are each independently chosen from
- (i) hydrogen; and
- (ii) $C_1$-$C_5$ alkyl radicals optionally substituted by at least one group chosen from hydroxyl, $C_1$-$C_3$ alkoxy, amino, $C_1$-$C_3$ alkylamino, di($C_1$-$C_3$) alkylamino, aminocarbonyl, —COOH, —SO$_3$H, tri($C_1$-$C_3$)alkylammonium, and $C_1$-$C_3$ alkylimidazolium.

6. The at least one entity according to claim 1, wherein X is chosen from pyrrolidinyl groups optionally substituted by at least one group chosen from tri($C_1$-$C_3$)alkylammonium and $C_1$-$C_3$ alkylimidazolium.

7. The at least one entity according to claim 1, chosen from:

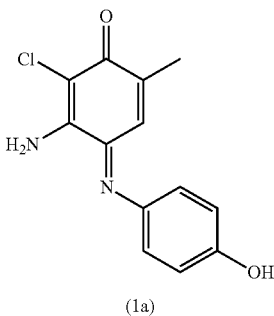

3-Amino-2-chloro-4-(4-hydroxyphenylimino)-6-methylcyclohexa-2,5-dienone (1a)

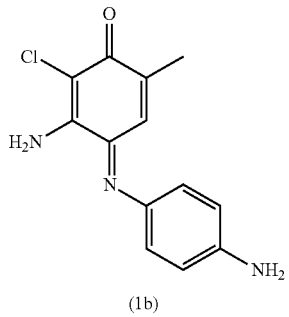

3-Amino-4-(4-aminophenylimino)-2-chloro-6-methylcyclohexa-2,5-dienone (1b)

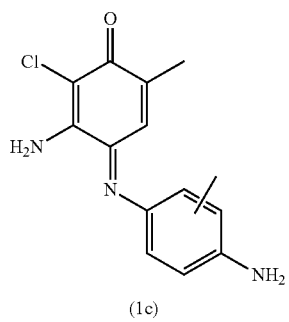
(1c)
3-Amino-4-(4-amino-methylphenylimino)-2-chloro-6-methylcyclohexa-2,5-dienone
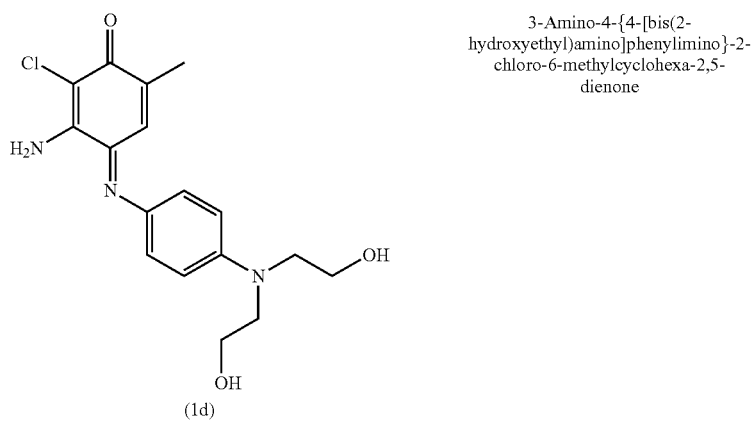
(1d)
3-Amino-4-{4-[bis(2-hydroxyethyl)amino]phenylimino}-2-chloro-6-methylcyclohexa-2,5-dienone
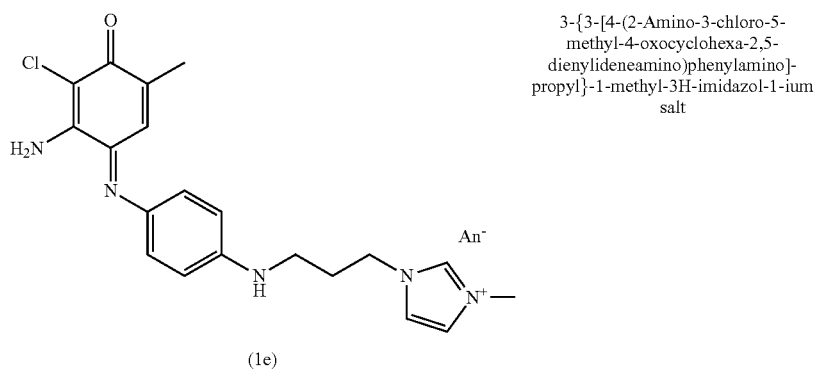
(1e)
3-{3-[4-(2-Amino-3-chloro-5-methyl-4-oxocyclohexa-2,5-dienylideneamino)phenylamino]-propyl}-1-methyl-3H-imidazol-1-ium salt
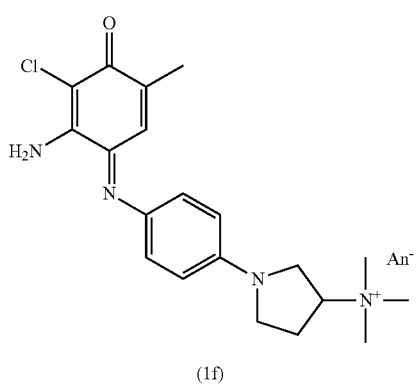
(1f)
{1-[4-(2-Amino-3-chloro-5-methyl-4-oxocyclohexa-2,5-dienylideneamino)phenyl]-pyrrolidin-3-yl}trimethylammonium salt

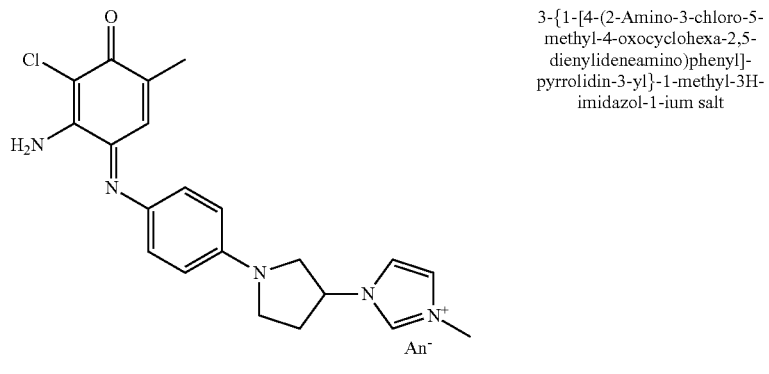

3-{1-[4-(2-Amino-3-chloro-5-methyl-4-oxocyclohexa-2,5-dienylideneamino)phenyl]-pyrrolidin-3-yl}-1-methyl-3H-imidazol-1-ium salt (1g)

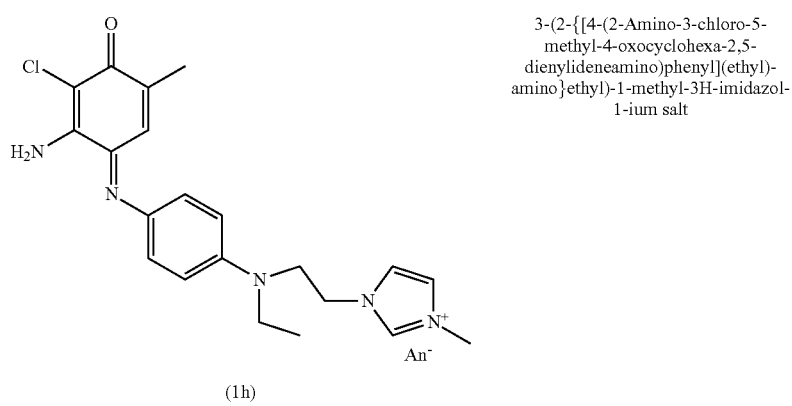

3-(2-{[4-(2-Amino-3-chloro-5-methyl-4-oxocyclohexa-2,5-dienylideneamino)phenyl](ethyl)-amino}ethyl)-1-methyl-3H-imidazol-1-ium salt (1h)

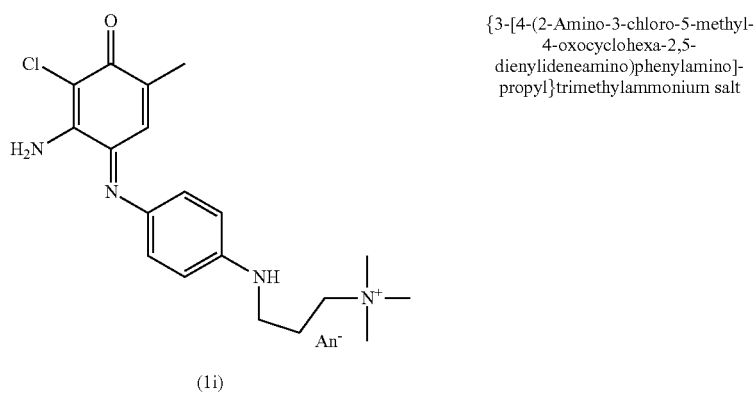

{3-[4-(2-Amino-3-chloro-5-methyl-4-oxocyclohexa-2,5-dienylideneamino)phenylamino]-propyl}trimethylammonium salt (1i)

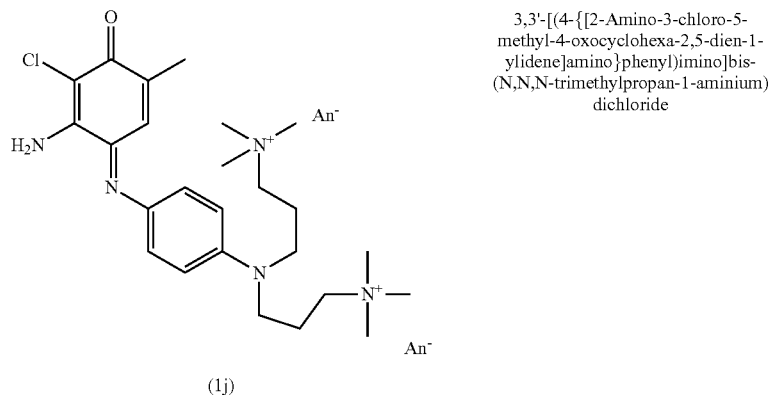

3,3'-[(4-{[2-Amino-3-chloro-5-methyl-4-oxocyclohexa-2,5-dien-1-ylidene]amino}phenyl)imino]bis-(N,N,N-trimethylpropan-1-aminium) dichloride (1j)

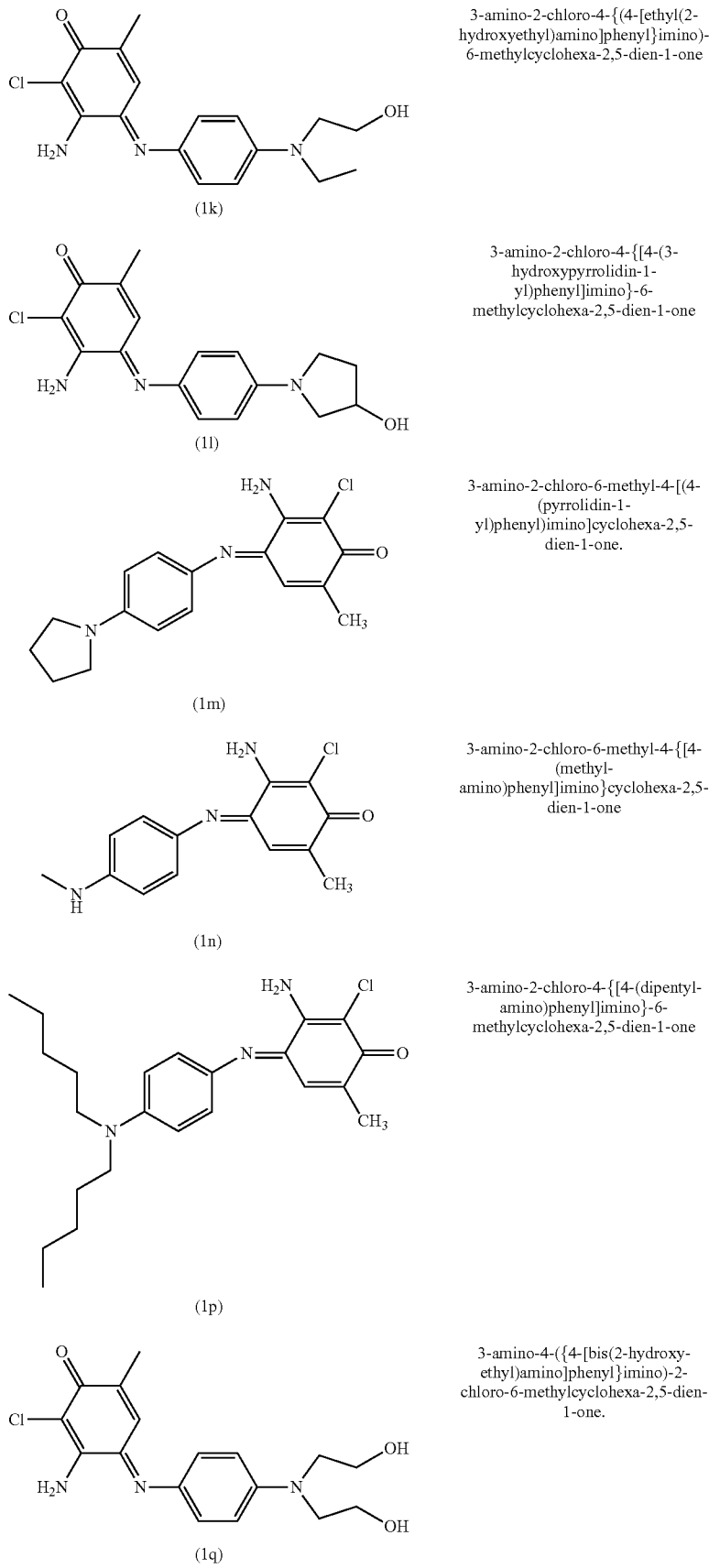

| | |
|---|---|
| (1k) | 3-amino-2-chloro-4-{(4-[ethyl(2-hydroxyethyl)amino]phenyl}imino)-6-methylcyclohexa-2,5-dien-1-one |
| (1l) | 3-amino-2-chloro-4-{[4-(3-hydroxypyrrolidin-1-yl)phenyl]imino}-6-methylcyclohexa-2,5-dien-1-one |
| (1m) | 3-amino-2-chloro-6-methyl-4-[(4-(pyrrolidin-1-yl)phenyl)imino]cyclohexa-2,5-dien-1-one. |
| (1n) | 3-amino-2-chloro-6-methyl-4-{[4-(methyl-amino)phenyl]imino}cyclohexa-2,5-dien-1-one |
| (1p) | 3-amino-2-chloro-4-{[4-(dipentyl-amino)phenyl]imino}-6-methylcyclohexa-2,5-dien-1-one |
| (1q) | 3-amino-4-({4-[bis(2-hydroxy-ethyl)amino]phenyl}imino)-2-chloro-6-methylcyclohexa-2,5-dien-1-one. |

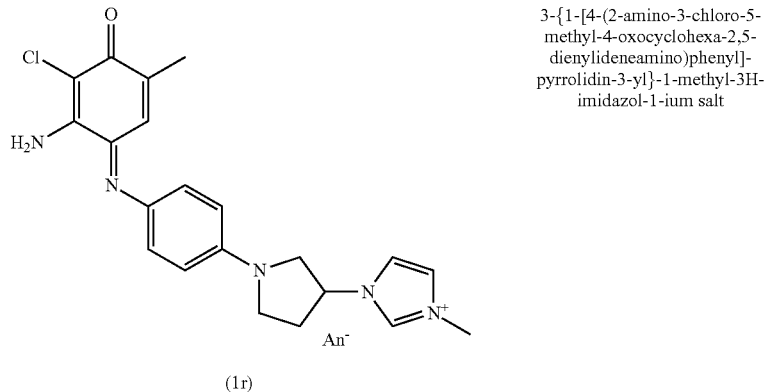

3-{1-[4-(2-amino-3-chloro-5-methyl-4-oxocyclohexa-2,5-dienylideneamino)phenyl]-pyrrolidin-3-yl}-1-methyl-3H-imidazol-1-ium salt (1r)

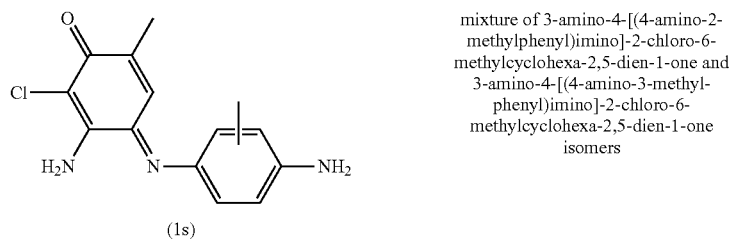

mixture of 3-amino-4-[(4-amino-2-methylphenyl)imino]-2-chloro-6-methylcyclohexa-2,5-dien-1-one and 3-amino-4-[(4-amino-3-methyl-phenyl)imino]-2-chloro-6-methylcyclohexa-2,5-dien-1-one isomers (1s)

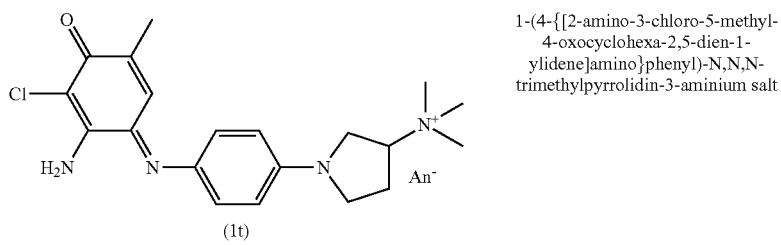

1-(4-{[2-amino-3-chloro-5-methyl-4-oxocyclohexa-2,5-dien-1-ylidene]amino}phenyl)-N,N,N-trimethylpyrrolidin-3-aminium salt (1t)

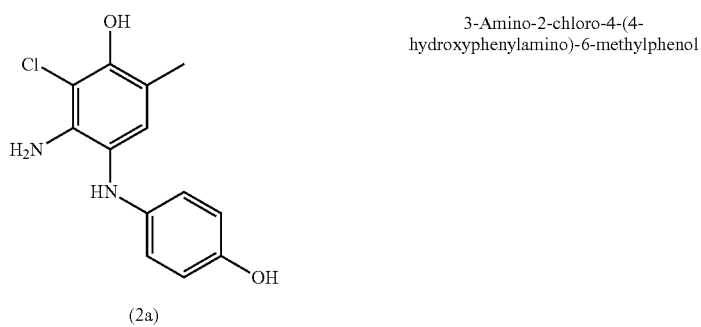

3-Amino-2-chloro-4-(4-hydroxyphenylamino)-6-methylphenol (2a)

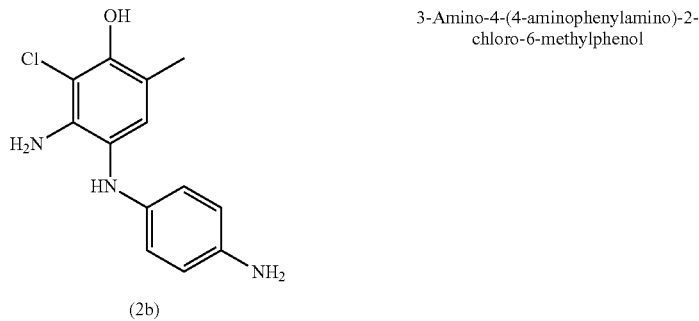

3-Amino-4-(4-aminophenylamino)-2-chloro-6-methylphenol (2b)

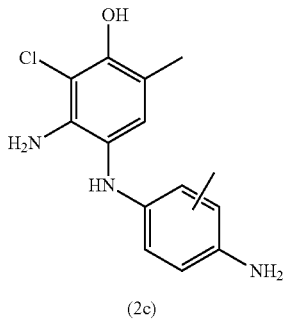
3-Amino-4-(4-amino-methylphenylamino)-2-chloro-6-methylphenol
(2c)
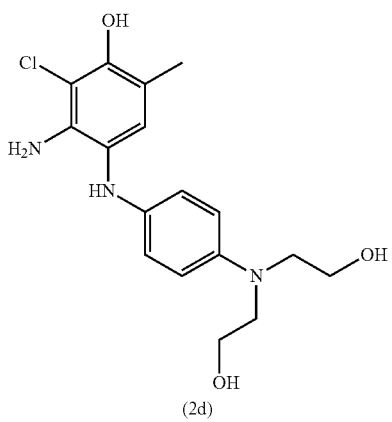
3-Amino-4-{4-[bis(2-hydroxyethyl)amino]phenylamino}-2-chloro-6-methylphenol
(2d)
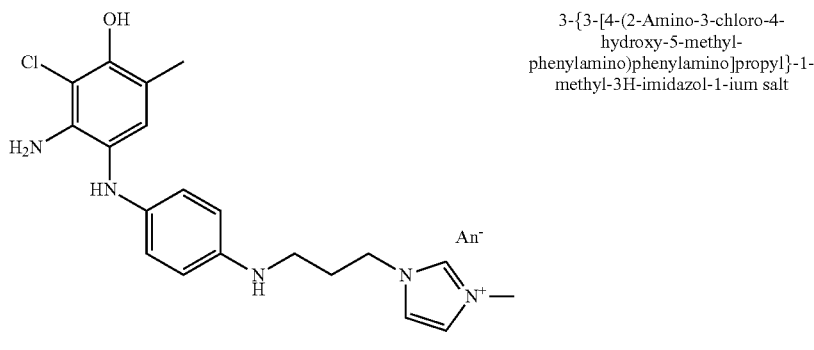
3-{3-[4-(2-Amino-3-chloro-4-hydroxy-5-methyl-phenylamino)phenylamino]propyl}-1-methyl-3H-imidazol-1-ium salt
(2e)
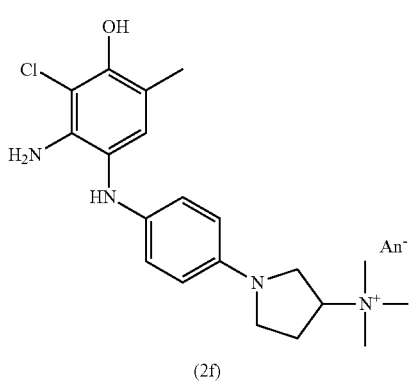
{1-[4-(2-Amino-3-chloro-4-hydroxy-5-methylphenylamino)phenyl]-pyrrolidin-3-yl}trimethyl-ammonium salt
(2f)

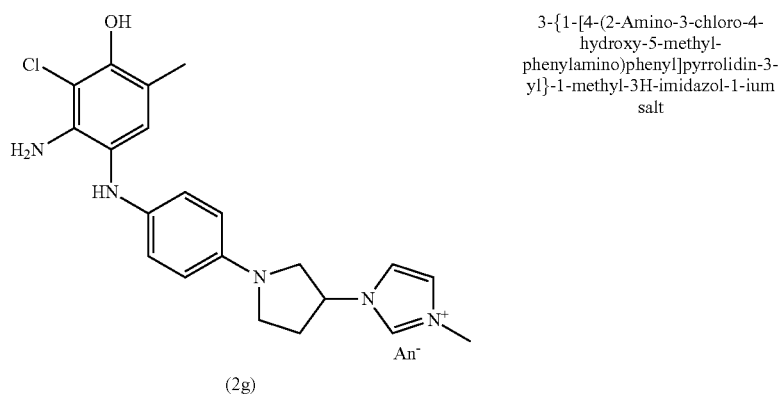

3-{1-[4-(2-Amino-3-chloro-4-hydroxy-5-methyl-phenylamino)phenyl]pyrrolidin-3-yl}-1-methyl-3H-imidazol-1-ium salt (2g)

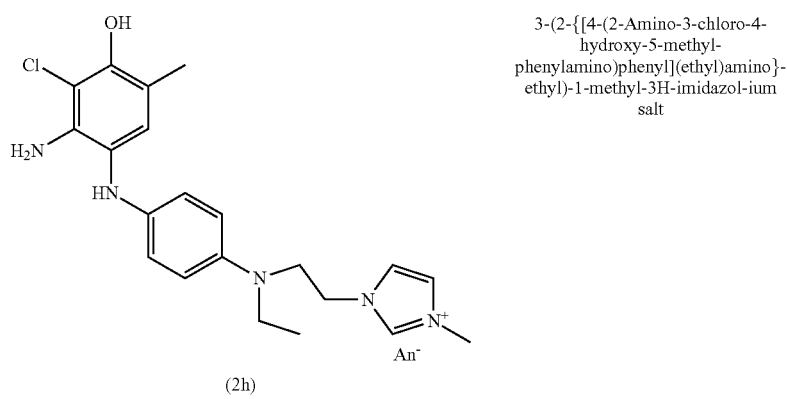

3-(2-{[4-(2-Amino-3-chloro-4-hydroxy-5-methyl-phenylamino)phenyl](ethyl)amino}-ethyl)-1-methyl-3H-imidazol-ium salt (2h)

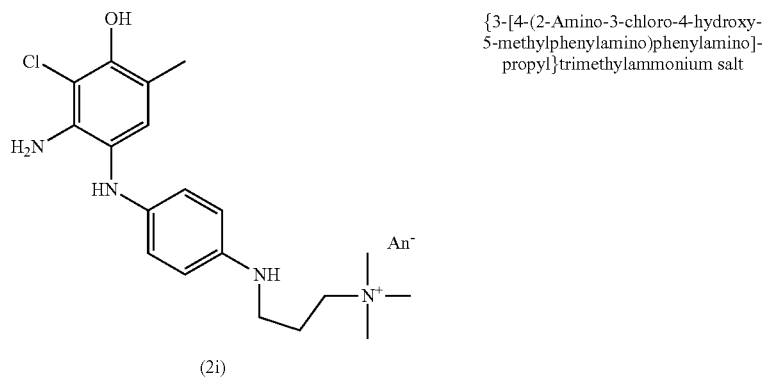

{3-[4-(2-Amino-3-chloro-4-hydroxy-5-methylphenylamino)phenylamino]-propyl}trimethylammonium salt (2i)

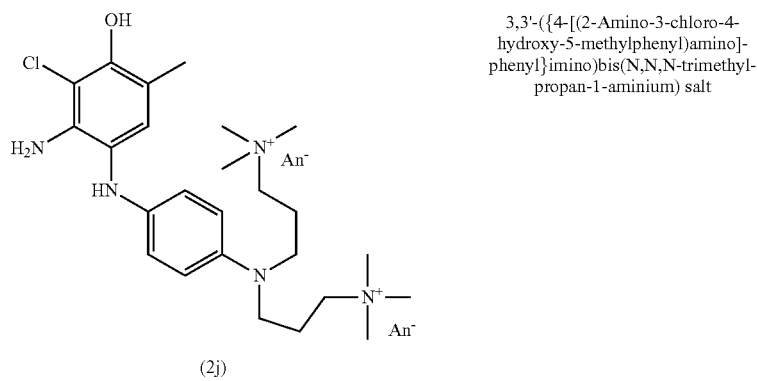

3,3'-({4-[(2-Amino-3-chloro-4-hydroxy-5-methylphenyl)amino]-phenyl}imino)bis(N,N,N-trimethyl-propan-1-aminium) salt (2j)

-continued

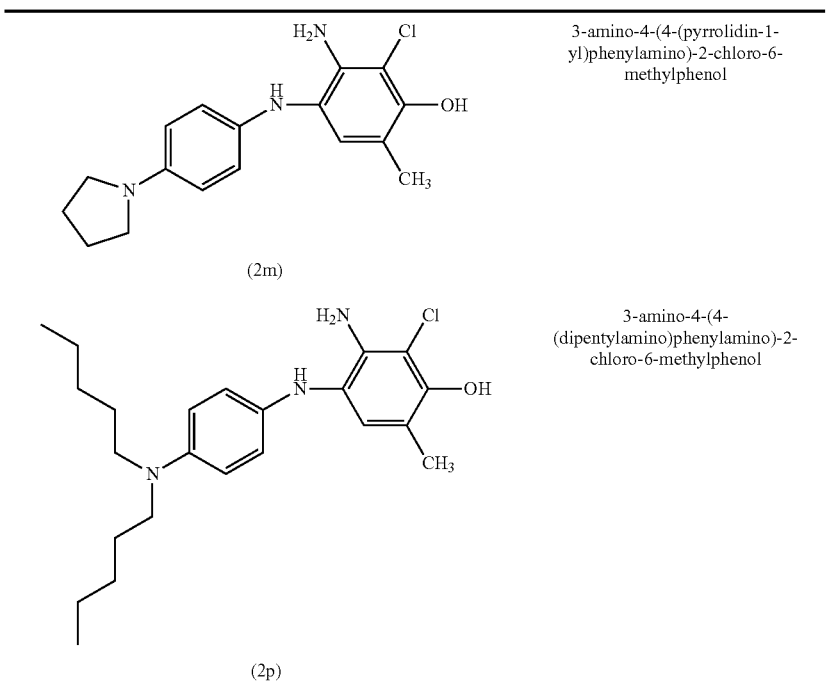

(2m) 3-amino-4-(4-(pyrrolidin-1-yl)phenylamino)-2-chloro-6-methylphenol (2p) 3-amino-4-(4-(dipentylamino)phenylamino)-2-chloro-6-methylphenol wherein An⁻ is independently chosen from cosmetically acceptable anionic counterions.

8. A dyeing composition comprising, in a cosmetically acceptable medium, at least one entity chosen from compounds of formula (I) and compounds of formula (II):

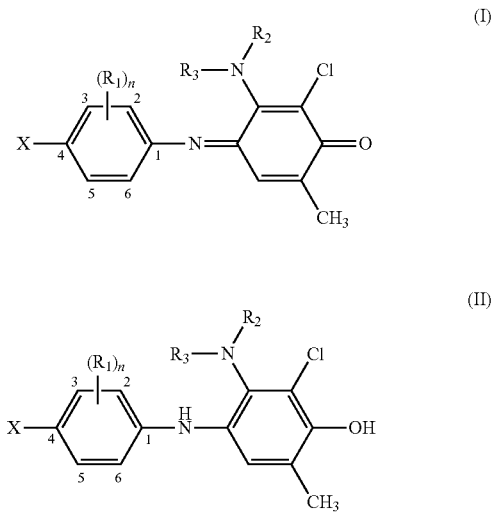

organic salts, inorganic salts, geometrical isomers, tautomers, and solvates thereof, wherein in formula (I) or formula (II):

$R_1$ is independently chosen from:
  chlorine;
  $C_1$-$C_3$ alkyl radicals optionally substituted by at least one hydroxyl group; and
  $C_1$-$C_3$ alkoxy radicals optionally substituted by at least one hydroxyl group;

X is independently chosen from:
  hydroxyl;
  $NR_4R_5$ radicals wherein $R_4$ and $R_5$ are each independently chosen from
    (i) hydrogen; and
    (ii) $C_1$-$C_5$ alkyl radicals optionally substituted by at least one group chosen from hydroxyl, $C_1$-$C_3$ alkoxy, amino, $C_1$-$C_3$ alkylamino, di($C_1$-$C_3$) alkylamino, aminocarbonyl, —COOH, —SO$_3$H, tri($C_1$-$C_3$)alkylammonium, and $C_1$-$C_3$ alkylimidazolium;
  pyrrolidinyl radicals optionally substituted by at least one group chosen from hydroxyl, $C_1$-$C_3$ alkoxy, amino, $C_1$-$C_3$ alkylamino, di($C_1$-$C_3$) alkylamino, tri($C_1$-$C_3$)alkylammonium, and $C_1$-$C_3$ alkylimidazolium; and
  piperidinyl radicals optionally substituted by at least one group chosen from hydroxyl, $C_1$-$C_3$ alkoxy, amino, $C_1$-$C_3$ alkylamino, di($C_1$-$C_3$) alkylamino, tri($C_1$-$C_3$) alkylammonium, and $C_1$-$C_3$ alkylimidazolium;
n is an integer chosen from 0, 1, 2, and 3;
$R_2$ and $R_3$ are independently chosen from:
  (i) hydrogen; and
  (ii) $C_1$-$C_5$ alkyl radicals optionally substituted by at least one group chosen from hydroxyl, $C_1$-$C_3$ alkoxy, amino, $C_1$-$C_3$ alkylamino, di($C_1$-$C_3$) alkylamino, aminocarbonyl, —COOH, —SO$_3$H, tri($C_1$-$C_3$)alkylammonium, and $C_1$-$C_3$ alkylimidazolium;
wherein when at least one of X, $R_2$, $R_3$, $R_4$, and $R_5$ comprises a cationic group, the electrical neutrality of the at least one entity is achieved by at least one cosmetically acceptable anionic counterion.

9. The dyeing composition according to claim 8, wherein the at least one entity is present in an amount ranging from 0.001% to 30% by weight, relative to the weight of the total composition.

10. The dyeing composition according to claim 8, wherein the composition comprises at least one compound of formula (I) and the composition has a pH of between 6 and 11.

11. The dyeing composition according to claim 8, wherein the composition comprises at least one compound of formula (II) and the composition has a pH of between 6 and 11.

12. The dyeing composition according to claim 8, further comprising at least one oxidizing agent.

13. The dyeing composition according to claim 12, wherein the at least one oxidizing agent is chosen from hydrogen peroxide, urea hydrogen peroxide, alkali metal bromates, persalts, peracids, and oxidase enzymes.

14. The dyeing composition according to claim 8, further comprising at least one direct dye different from the at least one entity and chosen from neutral, acid, and cationic nitrobenzene direct dyes; neutral, acid, and cationic azo direct dyes;
tetraazapentamethine dyes; neutral, acidic, and cationic quinone dyes; azine direct dyes; triarylmethane direct dyes; indoamine direct dyes; and natural direct dyes.

15. The dyeing composition according to claim 8, further comprising at least one adjuvant chosen from anionic, cationic, nonionic, amphoteric, and zwitterionic surface-active agents; anionic, cationic, nonionic, amphoteric, and zwitterionic polymers; inorganic and organic thickening agents; antioxidants; penetrating agents; sequestering agents; fragrances; buffers; dispersing agents; conditioning agents; film-forming agents; ceramides; preservatives; opacifying agents; and conducting polymers.

16. A method for dying keratinous fibers comprising applying to the keratinous fibers a dyeing composition comprising, in a cosmetically acceptable medium, at least one entity chosen from compounds of formula (I) and compounds of formula (II):

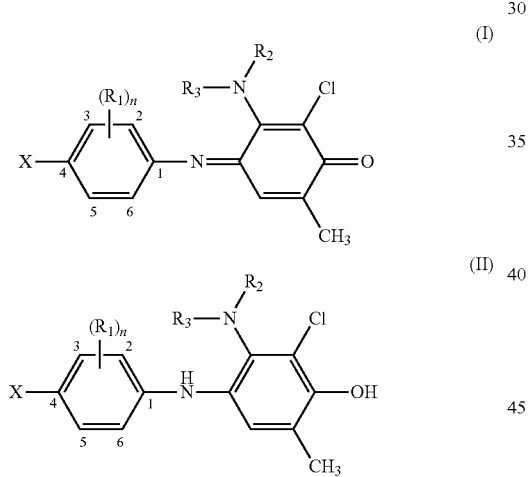

organic salts, inorganic salts, geometrical isomers, tautomers, and solvates thereof, wherein in formula (I) or formula (II):

$R_1$ is independently chosen from:

chlorine;

$C_1$-$C_3$ alkyl radicals optionally substituted by at least one hydroxyl group; and $C_1$-$C_3$ alkoxy radicals optionally substituted by at least one hydroxyl group;

X is independently chosen from:

hydroxyl;

$NR_4R_5$ radicals wherein $R_4$ and $R_5$ are each independently chosen from (i) hydrogen; and (ii) $C_1$-$C_5$ alkyl radicals optionally substituted by at least one group chosen from hydroxyl, $C_1$-$C_3$ alkoxy, amino, $C_1$-$C_3$ alkylamino, di($C_1$-$C_3$) alkylamino, aminocarbonyl, —COOH, —SO$_3$H, tri($C_1$-$C_3$)alkylammonium, and $C_1$-$C_3$ alkylimidazolium;

pyrrolidinyl radicals, optionally substituted by at least one group chosen from hydroxyl, $C_1$-$C_3$ alkoxy, amino, $C_1$-$C_3$ alkylamino, di($C_1$-$C_3$) alkylamino, tri($C_1$-$C_3$)alkylammonium, and $C_1$-$C_3$ alkylimidazolium; and piperidinyl radicals optionally substituted by at least one group chosen from hydroxyl, $C_1$-$C_3$ alkoxy, amino, $C_1$-$C_3$ alkylamino, di($C_1$-$C_3$) alkylamino, tri($C_1$-$C_3$) alkylammonium, and $C_1$-$C_3$ alkylimidazolium;

n is an integer chosen from 0, 1, 2, and 3;

$R_2$ and $R_3$ are independently chosen from:

(i) hydrogen; and (ii) $C_1$-$C_5$ alkyl radicals optionally substituted by at least one group chosen from hydroxyl, $C_1$-$C_3$ alkoxy, amino, $C_1$-$C_3$ alkylamino, di($C_{1\text{-}C3}$) alkylamino, aminocarbonyl, —COOH, —SO$_3$H, tri($C_1$-$C_3$)alkylammonium, and $C_1$-$C_3$ alkylimidazolium;

wherein when at least one of X, $R_2$, $R_3$, $R_4$, and $R_5$ comprises a cationic group, the electrical neutrality of the at least one entity is achieved by at least one cosmetically acceptable anionic counterion.

* * * * *

UNITED STATES PATENT AND TRADEMARK OFFICE
CERTIFICATE OF CORRECTION

PATENT NO. : 8,083,809 B2  
APPLICATION NO. : 12/808100  
DATED : December 27, 2011  
INVENTOR(S) : Madeleine Leduc et al.

Page 1 of 1

It is certified that error appears in the above-identified patent and that said Letters Patent is hereby corrected as shown below:

Claim 1, col. 35, line 15, "alkyl radical" should read -- alkyl radicals --.

Claim 1, col. 35, line 17, "alkoxy radical" should read -- alkoxy radicals --.

Claim 1, col. 35, line 24, " ii) a $C_1$-$C_5$ alkyl radical" should read -- ii) $C_1$-$C_5$ alkyl radicals --.

Claim 1, col. 35, line 30, "pyrrolidinyl radical" should read -- pyrrolidinyl radicals --.

Claim 1, col. 35, line 33, insert -- and -- after -- alkylimidazolium; --.

Claim 1, col. 35, line 34, "a piperidinyl radical" should read -- piperidinyl radicals --

Claim 1, col. 36, line 7, "ii) a $C_1$-$C_5$ alkyl radical" should read -- ii) $C_1$-$C_5$ alkyl radicals --.

Claim 1, col. 36, line 12, "wherein at least" should read -- wherein when at least --.

Claim 1, col. 36, line 12, delete second instance of "$R_2$".

Claim 1, col. 36, line 12, "comprise" should read -- comprises --.

Claim 16, col. 52, line 40, "di($C_1$-$C_3$)" should read -- di($C_1$-$C_3$) --.

Signed and Sealed this  
Seventeenth Day of April, 2012

David J. Kappos  
*Director of the United States Patent and Trademark Office*